US012698472B2

(12) United States Patent
Paez et al.

(10) Patent No.: US 12,698,472 B2
(45) Date of Patent: Aug. 4, 2026

(54) HYDROGELS

(71) Applicant: Leibniz-Institut für Neue Materialien gemeinnützige GmbH, Saarbrücken (DE)

(72) Inventors: Julieta I. Paez, Saarbrücken (DE); Aleeza Farrukh, Irvine, CA (US); Aránzazu del Campo, Mainz-Bretzenheim (DE)

(73) Assignee: Leibniz-Institut für Neue Materialien gemeinnützige GmbH, Saarbrücken (DE)

( * ) Notice: Subject to any disclaimer, the term of this patent is extended or adjusted under 35 U.S.C. 154(b) by 933 days.

(21) Appl. No.: 17/621,734

(22) PCT Filed: Jun. 23, 2020

(86) PCT No.: PCT/EP2020/067410
§ 371 (c)(1),
(2) Date: Dec. 22, 2021

(87) PCT Pub. No.: WO2021/001203
PCT Pub. Date: Jan. 7, 2021

(65) Prior Publication Data

US 2022/0235316 A1 Jul. 28, 2022

(30) Foreign Application Priority Data

Jul. 3, 2019 (DE) ..................... 10 2019 117 997.1

(51) Int. Cl.
*C12N 5/00* (2006.01)
*C08J 3/075* (2006.01)
*C08J 3/24* (2006.01)
*C12N 5/077* (2010.01)

(52) U.S. Cl.
CPC ............ *C12N 5/0012* (2013.01); *C08J 3/075* (2013.01); *C08J 3/246* (2013.01); *C12N 5/0062* (2013.01); *C12N 5/0656* (2013.01); *C08J 2300/206* (2013.01); *C08J 2371/02* (2013.01)

(58) Field of Classification Search
CPC .. C12N 5/0012; C12N 5/0062; C12N 5/0656; C08J 3/075; C08J 3/246
See application file for complete search history.

(56) References Cited

U.S. PATENT DOCUMENTS

2003/0162841 A1 8/2003 Pathak et al.
2019/0105395 A1* 4/2019 Alsberg .................. C08J 3/246

OTHER PUBLICATIONS

Translation of International Preliminary Report on Patentability, Jan. 13, 2022.

(Continued)

*Primary Examiner* — John E Uselding
(74) *Attorney, Agent, or Firm* — CAHN & SAMUELS, LLP

(57) ABSTRACT

A process for preparing a hydrogel includes a) preparing a composition comprising a1) at least one macromer comprising as functional groups at least two thiol groups, and a2) at least one macromer comprising as functional groups at least two aromatic or heteroaromatic groups each substituted by at least one sulfonyl group, wherein at least one component a1) or a2) has at least three of the functional groups; and b) reacting the two macromers a1) and a2) via the functional groups to form a hydrogel.

18 Claims, 13 Drawing Sheets

(56) References Cited

OTHER PUBLICATIONS

International Search Report for Application No. PCT/EP2020/067410, Oct. 9, 2020.
Boehnke, et al., "Imine Hydrogels with Tunable Degradability for Tissue Engineering", Biomacromolecules, 2015, vol. 16, 2101-2108.
Chen, et al., "Discover of Heteroaromatic Sulfones As a New Class of Biologically Compatible Thiol-Selective Reagents", ACS Chemical Biology, 2017, vol. 12, 2201-2208.
DeForest, et al., "Cytocompatible Click-based Hydrogels with Dynamically-Tunable Properties Through Orthogonal Photoconjugation and Photocleavage Reactions", Nat. Chem., 2012, vol. 3, No. 12, 925-931.
Farrukh, et al., "Bioconjugating Thiols to Poly(acrylamide) Gets for Cell Culture Using Methylsulfonyl Co-monomers", Angewandte Chemie Int. Ed., vol. 55, 2016, 2092-2096.
Farrukh, et al., "4D Biomaterials for Light-Guided Angiogenesis", Advanced Functional Materials, 1807734, 2018, 1-11.
Farrukh, et al., Biofunctional Poly(acrylamide) Hydrogels Through Orthogonal Coupling Chemistries, Biomacromolecules, 2017, vol. 18, 906-913.
Jansen, et al., "Control of Thiol-Maleimide Reaction Kinetics in PEG Hydrogel Networks", Acta Biomaterialia, 2018, vol. 70, 120-128.
Kharkar, et al., "Thiol-ene Click Hydrogels for Therapeutic Delivery", ACS Biomaterials Science & Engineering, 2016, vol. 2, 165-179.
Kim, et al., Characterization of The Crossing Kinetics of Multi-Arm Poly(Ethylene Glycol) Hydrogels Formed via Michael-Type Addition, Soft Matter, 2016, vol. 12, 2076-2085.
Zheng, et al., "Intracellular Synthesis of D-Aminoluciferin for Bioluminescence Generation", Chem. Commun., 2017, vol. 53, 3567-3570.
Zhao, et al., "Targted Delivery of an Activatable Fluorescent Probe for The Detection of Furin Activity in Living Cells", ChemBioChem, 2018, vol. 19, 1060-1075.
Lutolf, et al., "Cells-Responsive Synthetic Hydrogels", Advanced Materials, 2003, vol. 15, No. 11, 888-892.
Phelps, et al., "Maleimide Cross-Linked Bioactive PEG Hydrogel Exhibits Improved Reaction Kinetics and Cross-Linking for Cell Encapsulation and In Situ Delivery", Advanced Materials, vol. 24, 2011, 64-70.
Saito, et al., "Critical Evaluation and Rate Constants of Chemoselective Ligation Reactions for Stoichiometric Conjugations in Water", ACS Chemical Biology, 2015, vol. 10, 1026-1033.
Stenzel, "Bioconjugation Using Thiols: Old Chemistry to Connect Polymers with Nature's Building Blocks", ACS Macro Lett., 2013, 2, 14-18.
Toda, et al., "Rapid, Stable, Chemoselective Labeling of Thiols with Julia-Kocieński Like Reagents: A Serum-Stable Alternative to Maleimide-Based Protein Conjugation", Angewandte Chemie, vol. 52, 2013, 12592-12596.
Wang, et al., "Reactivity and Kinetics of Vinyl Sulfone-Functional Self-Assembled Monolayers for Bioactive Ligand Immobilization", Langmuir, 2015, vol. 31, 3413-3421.
Lee, et al., "Three-Dimensional Micropatterning of Bioactive Hydrogels via Two-Photon Laser Scanning Photolithography for Guided 3D Cell Migration", Biomaterials, 2008, vol. 29, 2962-2968.
Zhang, et al., "Methylsulfonyl Benzothiazole (MSBT): A Selective Protein Thiol Blocking Reagent", Organic Letters 2012, vol. 14, No. 13, 3396-3399.
Kharkar et al., "Design of thiol- and light-sensative degradable hydrogels using Michael-type addition reactions", Polymer Chemistry, 2015, 6, 5565-74.

* cited by examiner a)

b)

a)

b)

a)

b)

HYDROGELS

This patent application is a U.S. national stage application of PCT international application PCT/EP2020/067410 filed on 23 Jun. 2020 and claims priority of German patent document 10 2019 117 997.1 filed on 3 Jul. 2019, the entireties of which are incorporated herein by reference.

FIELD OF THE INVENTION

The invention relates to hydrogels, to processes for preparing them, and to their use.

BACKGROUND OF THE INVENTION

Hydrogels are three-dimensional networks of crosslinked hydrophilic polymers that include a high fraction of water. Known uses of such materials include matrix materials for biological applications such as active ingredient transport, wound materials, tissue engineering, and they can also be used in cell culture. Their aqueous and porous structure allows then to transport nutrients effectively to the cells.

Many natural or synthetic polymers have already been used for the preparation of hydrogels, examples being collagen, gelatin and polyethylene glycol (PEG). For the crosslinking of the hydrogels, various reactions and mechanisms have been studied, examples being photopolymerization, Michael addition or the like.

Controlling the crosslinking reaction, specifically, is a major challenge. Especially so if the hydrogel is to be produced for the purpose of enveloping cells. If the gel polymerizes too rapidly, it is often not uniformly crosslinked. If it polymerizes too slowly, the constituents to be enclosed, cells for example, may undergo settlement and are not uniformly enclosed.

It is an object of the invention to provide a process for preparing a hydrogel that allows use in particular for enveloping cells. A further object is to provide such a hydrogel and its use.

SUMMARY OF THE INVENTION

This object is achieved by the inventions having the features of the independent claims. Advantageous developments of the inventions are characterized in the dependent claims. The wording of all of the claims is hereby made part of the content of this description through reference. The inventions also embrace all rational combinations, and more particularly all stated combinations, of independent and/or dependent claims.

A process for preparing a hydrogel, comprising the following steps:

- a) preparing a composition comprising
  - a1) at least one macromer comprising as functional groups at least two thiol groups,
  - a2) at least one macromer comprising as functional groups at least two aromatic or heteroaromatic groups each substituted by at least one sulfonyl group, where at least one component a1) or a2) contains at least three of the stated functional groups;
- b) reacting the two macromers via the functional groups to form a hydrogel.

Individual process steps are described in more detail below. The steps need not necessarily be performed in the specified order, and the process to be outlined may also contain further steps, not stated.

A macromer is understood to be a compound which has an average molar mass of less than 500 kDa, preferably of less than 100 kDa, more particularly of less than 50 kDa. The average molar mass is determined as weight-average molecular weight by gel permeation chromatography (GPC).

Particularly preferred macromers are those having an average molar mass of less than 50 kDa, more particularly of less than 30 kDa.

In one particular embodiment of the invention the average molar mass of a macromer is between 100 Da and 500 kDa, preferably between 200 Da and 200 kDa, more particularly between 800 Da and 100 kDa.

It is important here that the macromer carries the corresponding functional groups and that these groups are available for the reaction.

Preferred macromers in this context are those containing 2, 3, 4, 5, 6, 7, 8, 9 or 10 functional groups, preferably 2, 3, 4, 5, 6, 7, 8 functional groups, more preferably 2, 3, 4, 5 or 6 functional groups, more particularly containing 2, 3 or 4 functional groups.

"To form the hydrogel" means that a hydrogel is formed as a result of the crosslinking. Crosslinking reactions therefore take place to a sufficient extent. This can be controlled through the nature and amount of the components employed.

In another preferred embodiment at least one component a1) or a2) contains at least 4 of the stated functional groups.

In one preferred embodiment both components a1) and a2) contain at least 3, preferably at least 4, of the stated functional groups. More preferably both components a1) and a2) contain 3, 4, 5, 6, 7, 8, 9 or 10 functional groups, preferably 3, 4, 5, 6, 7, 8 functional groups, more preferably 3, 4, 5 or 6 functional groups, more particularly 3 or 4 functional groups.

Water-soluble macromers are preferred. This means that the macromers are present in solution to the required extent under the conditions of the reaction.

Preferred macromers are those based on oligomers or polymers. These may be natural or synthetic oligomers or polymers. Examples of synthetic oligomers or polymers are poly(meth)acrylates such as poly(meth)acrylamides, poly(meth)acrylic acid, polyHPMA or polyHEMA, polyethylene glycol (PEG), polyvinyl alcohol (PVA), polyurethane (PU), polyvinylpyrrolidone (PVP), polyamides, poly(amidoamines) (PAMAMV), polyesters, polylactides, polyglycolic acid (PGA) or poly(lactide-co-glycolide) (PLGA), polyanhydrides, poly(ortho)esters, polyacetals, poloxamers (block copolymers of ethylene oxide (PEG) and propylene oxide (PPG)) such as PEG-Co-PPG-Co-PEG), poly-2-oxazolines, polyphosphazenes, polyglycerol, polyamines such as polylysine or polyethylenimine (PEI), polycarbonates, polyglutamic acid, more particularly poly-gamma-glutamic acid, polyaspartic acid (PASA), polyphosphonates, or natural oligomers such as DNA, RNA, gelatin, polyhydroxyalkanoates (PHA), poly-gamma-glutamic acid, proteins or peptides such as collagens, VPM, albumin or fibrin, polysaccharides such as agarose, chitin, chitosan, chondroitin, mannan, inulin, dextran, cellulose, alginates or hyaluronic acid. Preferred oligomers are those based on polyethylene glycol. The oligomers and polymers are functionalized with the corresponding functional groups.

In the case of the peptide-based oligomers, the thiol groups are provided preferably through the corresponding amino acids such as cysteine or homocysteine. "Peptide-based" here means that the oligomer in question is constructed to an extent of at least 80% of the molecular mass from natural or nonnatural amino acids. Such oligomers therefore contain at least two thiol groups, more particularly at least two cysteine.

The at least partial use of natural polymers also allows the introduction of specifically cleavable sites in the hydrogel, through enzymes, for example.

It may be necessary for the functional groups to be bound to the oligomer or polymer via a short linker, for example via one or more esters, ethers or amide bonds. Preferred linkers are those having a molar mass of less than 1500 mol, preferably of less than 800 mol, more particularly less than 500 mol or less than 200 mol.

The thiol groups are preferably in the form of free thiol groups. It is also possible for them to carry groups which are eliminated before the hydrogel is formed.

The macromer a2) is a macromer comprising at least two aromatic groups each substituted by at least one sulfonyl group. Preferred groups are those of the formula (1):

$$M—Ar—SO_2—R^1 \quad (1)$$

where Ar is an electron-deficient aryl group or electron-deficient heteroaryl group. Consequently it is possible to select reaction conditions under which the thiol groups of the first macromer are able to perform a nucleophilic aromatic substitution on the group Ar, with the group $SO_2$—$R^1$ serving as leaving group.

M is a preferably covalent connection to the macromer and is preferably a single bond, ether, or carbonyl group. The carbonyl group may be part of an ester or amide bond. As group Ar it is possible accordingly to use the corresponding esters or amides for coupling to the macromer, such as correspondingly substituted benzoic esters or benzoic amides, for example.

An aryl group in the sense of this invention contains 6 to 40 C atoms; a heteroaryl group in the sense of this invention contains 1 to 40 C atoms and at least one heteroatom, with the proviso that the sum total of C atoms and heteroatoms makes at least 5. The heteroatoms are preferably selected from N, O and/or S. An aryl group or heteroaryl group here refers to either a single aromatic ring, i.e., benzene, or a single heteroaromatic ring, such as pyridine, pyrimidine, thiophene, etc., or a fused aryl or heteroaryl group, such as naphthalene, naphthalimide, anthracene, quinoline, isoquinoline, etc.

An electron-deficient aryl group or heteroaryl group refers to an aryl group or heteroaryl group whose I-electron density is reduced as a result of negative induction effects or negative mesomeric effects (—I effects or -M effects). A listing of substituents or groups which bring about these effects is found in any standard textbook of organic chemistry. Examples that may be given without restriction are, for —I substituents: OH, halogens, more particularly fluorine and chlorine, $NO_2$, unsaturated groups; and for -M substituents: $NO_2$, CN, aryl groups or heteroaryl groups. These electron-withdrawing groups (EWG) must of course be in conjugation with the leaving group —$SO_2$—$R^1$, i.e., in ortho- or para-position in the case of carbocyclic systems, in order to be able to exert the desired effect. In the case of heteroaryl groups, the heteroatoms contribute to reducing the electron density correspondingly as a function of their position. Two or more different groups may also be present.

Examples of electron-deficient aryl groups are nitrobenzenes, benzaldehydes, benzonitriles, benzoesters, which may be substituted additionally by one or more groups $R^2$ as defined below.

Examples of an aryl group of this kind are compounds based on nitrobenzoic acid with 1 or 2 nitro groups, examples being nitrobenzoic esters or nitrobenzoic amides containing a group —$SO_2$—$R^1$ at one position at least. This group is preferably arranged in meta-position to a nitro group. Particular preference is given to a nitro group in 3-position and the —$SO_2$—$R^1$ group in 4-position. An example of such a compound is 3-nitro-4-sulfomethylbenzoic acid.

Examples of electron-deficient heteroaryl groups are, for example, monocyclic heteroaromatics such as pyridines, pyrimidines, pyrazines, pyridazines, triazines, such as 1,3,5-triazine, 1,2,4-triazine or 1,2,3-triazine, tetrazines, such as 1,2,4,5-tetrazine, 1,2,3,4-tetrazine or 1,2,3,5-tetrazine, oxazoles, isoxazole, thiazoles, such as 1,2-thiazole or 1,3-thiazole, isothiazole, oxadiazoles, such as 1,2,3-oxadiazole, 1,2,4-oxadiazole, 1,2,5-oxadiazole and 1,3,4-oxadiazole, thiadiazoles, such as 1,2,3-thiadiazole, 1,2,4-thiadiazole, 1,2,5-thiadiazole or 1,3,4-thiadiazole, imidazole, pyrazole, triazoles, such as more particularly 1,2,4-triazole or 1,2,3-triazole, tetrazole, polycyclic heteroaromatics, such as quinolines, isoquinolines, naphthalimide, benzimidazole, benzoxazole, benzothiazole, benzopyridazine, benzopyrimidine, quinoxaline, benzotriazole, purine, pteridine, indolizine and benzothiadiazole, which may be substituted additionally by one or more groups $R^2$ as defined below.

Preferred heteroaryl groups are oxadiazoles and benzothiazole.

In one preferred embodiment of the invention Ar is a polycyclic heteroaryl group or a monocyclic heteroaryl group which is substituted by at least one further aryl group or heteroaryl group, preferably phenyl.

In another particularly preferred embodiment Ar is an oxadiazole group, more particularly a 1,3,4-oxadiazole group, which is preferably substituted by at least one phenyl group, more particularly by one phenyl group.

In another embodiment Ar is an aryl group which bears at least one —I or -M substituent, preferably 1 or 2, preferably F or $NO_2$, more preferably $NO_2$.

$R^1$ is $N(R^2)_2$, a straight-chain alkyl group having 1 to 20 C atoms or a branched or cyclic alkyl group having 3 to 20 C atoms, or an alkenyl or alkynyl group having 2 to 20 C atoms or a branched or cyclic alkyl group having 3 to 20 C atoms, where the alkyl, alkenyl or alkynyl group may be substituted in each case by one or more radicals $R^2$ and where one or more nonadjacent $CH_2$ groups may be replaced by O, $NR^2$, S, $R^2C{=}CR^2$, C≡C, C=O, C(=O)O or C(=O)$NR^2$, or is an aryl group or heteroaryl group which may be substituted in each case by one or more radicals $R^2$.

$R^2$, identical or different at each occurrence, is H, D, F, Cl, Br, I, $N(R^3)_2$, CN, $NO_2$, $OR^3$, $SR^3$, C(=O)$OR^3$, C(=O)N$(R^3)_2$, C(=O)$R^3$, a straight-chain alkyl group having 1 to 20 C atoms or an alkenyl or alkynyl group having 2 to 20 C atoms or a branched or cyclic alkyl group having 3 to 20 C atoms, where the alkyl, alkenyl or alkynyl group may be substituted in each case by one or more radicals $R^3$, where one or more nonadjacent $CH_2$ groups may be replaced by $R^3C{=}CR^3$, C≡C, C=O, $NR^3$, O, S, C(=O)O or C(=O)$NR^3$, or is an aryl group or heteroaryl group which may be substituted in each case by one or more radicals $R^3$.

$R^3$, identical or different at each occurrence, is H, D, F, OH, or an aliphatic, aromatic and/or heteroaromatic organic radical, more particularly a straight-chain alkyl group having 1 to 20 C atoms, in which one or more H atoms may also be replaced by F.

In one preferred embodiment $R^1$ is $N(R^2)_2$, a straight-chain alkyl group having 1 to 10 C atoms or a branched or cyclic alkyl group having 3 to 10 C atoms, where the alkyl group may be substituted in each case by one or more radicals $R^2$ and where one or more nonadjacent $CH_2$ groups may be replaced by O, $NR^2$, S, C═O, C(═O)O or C(═O)$NR^2$, or an aryl group or heteroaryl group, which may be substituted in each case by one or more radicals $R^2$.

$R^2$, identical or different at each occurrence, is H, D, F, Cl, Br, I, $N(R^3)_2$, CN, $NO_2$, $OR^3$, $SR^3$, C(═O)$OR^3$, C(═O)N$(R^3)_2$, C(═O)$R^3$, a straight-chain alkyl group having 1 to 10 C atoms or an alkenyl or alkynyl group having 2 to 10 C atoms or a branched or cyclic alkyl group having 3 to 10 C atoms, where the alkyl, alkenyl or alkynyl group may be substituted in each case by one or more radicals $R^3$, where one or more nonadjacent $CH_2$ groups may be replaced by $R^3C$═$CR^3$, C≡C, C═O, $NR^3$, O, S, C(═O)O or C(═O)$NR^3$, or an aryl group or heteroaryl group which may be substituted in each case by one or more radicals $R^3$.

$R^3$, identical or different at each occurrence, is H, D, F, OH or a straight-chain alkyl group having 1 to 5 C atoms, in which one or more H atoms may also be replaced by F or OH.

In one particularly preferred embodiment $R^1$ is $N(R^2)_2$, a straight-chain alkyl group having 1 to 6 C atoms or a branched or cyclic alkyl group having 3 to 6 C atoms, where the alkyl group may be substituted in each case by one or more radicals $R^2$ and where one or more nonadjacent $CH_2$ groups may be replaced by O, $NR^2$, S, C═O, C(═O)O or C(═O)$NR^2$, or an aryl group or heteroaryl group, having 5 to 10 aromatic ring atoms, which may be substituted in each case by one or more radicals $R^2$.

$R^2$, identical or different at each occurrence, is H, D, F, OH, C(═O)OH, a straight-chain alkyl group having 1 to 5 C atoms or an aryl group or heteroaryl group having 5 to 10 aromatic ring atoms, in which one or more H atoms bonded to carbon may also be replaced by F or $NO_2$.

More preferably $R^1$ is a substituted or unsubstituted methyl group, ethyl group, propyl group, preferably substituted by F or COOH, or is $N(R^2)_2$, more preferably is $NHR^2$, where $R^2$ is an aryl group or heteroaryl group having 5 to 10 ring atoms, in which one or more H atoms bonded to carbon may also be replaced by F, OH, $NH_2$ or $NO_2$. With more particular preference $R^1$ is methyl, $CH_2$—COOH or NH-phenyl, where the N is bonded to the $SO_2$ group.

In one preferred embodiment of the invention, at least one macromer is based on poly(meth)acrylates such as poly(meth)acrylamides, poly(meth)acrylic acid, polyHPMA or polyHEMA, polyethylene glycol (PEG), polyvinyl alcohol (PVA), polyurethane (PU), polyvinylpyrrolidone (PVP), polyamides, poly(amidoamines) (PAMAMV), polyesters, such as polylactides, polyglycolic acid (PGA) or poly(lactide-co-glycolide) (PLGA), polyanhydrides, poly(ortho)esters, polyacetals, poloxamers (block copolymers of ethylene oxide (PEG) and propylene oxide (PPG)) such as PEG-Co-PPG-Co-PEG), poly-2-oxazolines, polyphosphazenes, poly-glycerol, polyamines such as polylysine or polyethylenimine (PEI), polycarbonates, polyglutamic acid, more particularly poly-gamma-glutamic acid, polyaspartic acid (PASA), polyphosphonates, and the other macromer is based on DNA, RNA, gelatin, polyhydroxyalkanoates (PHA), poly-gamma-glutamic acid, peptides such as collagens, VPM, albumin or fibrin, polysaccharides such as agarose, chitin, chitosan, chondroitin, mannan, inulin, dextran, cellulose, alginates or hyaluronic acid. Consequently it is possible to integrate a biochemical reactivity into the hydrogel, for example a cleavage or degradation capacity, such as through ester groups or carbonate groups in the macromer or through enzymatic reactions, for example. Examples of suitable peptides are, for example, enzymatically cleavable dithiol peptides such as VPM (sequence: GCRDVPMSMRGGDRCG).

With preference both macromers are used such that the number of the functional groups SH:Ar—$SO_2$—$R^1$ in the two macromers that contribute to the crosslinking is 2:1 to 1:2, preferably 1.5:1 to 1:1.5, more preferably 1.2:1 to 1:1.2, more particularly 1:1. Where two or more different compounds with the respective functional group are used, the figures are based on the total number of these groups, such as when using different compounds with thiol groups. For example, one thiol compound may be used for the modification, and another compound for the crosslinking.

Both macromers are preferably present in solution, preferably in aqueous solution. It may be necessary to adapt the pH, preferably by using a buffer.

In one preferred embodiment a first solution with the first macromer comprising thiol groups and a second solution with the second macromer comprising the aromatic sulfonyl group are provided. These two solutions are then combined with one another.

In one preferred embodiment the pH of the solutions of the macromers that are used, more particularly of the composition, is 6 to 9 (at 25° C.). The pH is adjusted preferably by means of a buffer, preferably with a buffer concentration between 5 mM to 100 mM. Examples of buffers are PBS or HEPES. By means of a relatively high buffer concentration it is possible to stabilize the pH in the gel when using high macromer concentrations, as the leaving group is able to act as an acid. Preference is given to a pH of 6 to 9, preferably 6.5 to 8, more preferably 6.6 to 7.5. As a result it is possible to establish the gelling time between for example 3 seconds (pH 8) to 3.5 minutes (pH 6.6) (measured at 25° C. with constant macromer concentration).

It is also possible to constitute the composition at a first pH before initiating the crosslinking reaction by changing the pH to a second pH. The crosslinking reaction is preferably at least greatly slowed at the first pH; accordingly, the first pH is preferably outside the ranges stated above. The second pH is preferably within one of the ranges stated above. The change in pH may also be achieved by placing the composition into a medium with corresponding pH. With preference the second pH is between 6 to 9, preferably 6.5 to 8, more preferably 6.6 to 7.5.

The reaction may also be initiated, or accelerated, by alteration in the pH.

In another preferred embodiment the macromer content of the composition is 1 to 30 wt %, preferably 3 to 15 wt %, more preferably 3 to 10 wt %, based on all of the macromers used.

The temperature when the hydrogel is formed is preferably between 20° C. and 45° C., preferably between 20° C. and 40° C.

The reaction described here for the formation of the hydrogels features a number of advantages. In contrast to known crosslinking reactions, it is neither particularly rapid not particularly slow under physiological conditions, and is instead amenable to control by factors including the pH. This permits cells or other substances such as peptides, enzymes, chemical compounds or the like to be encapsulated during formation of the gel. During formation of the gel the composition remains viscous for longer, allowing it to be mixed for longer at low shearing forces. This allows the cells to be distributed uniformly in the hydrogel without any need for further steps, such as turning of the gel in the course of curing.

The proposed reaction is also sufficiently rapid under physiological conditions. This allows it to be used in cell cultures, preferably in three-dimensional cell cultures or even in situ. Gelling may also be controlled via the pH, allowing it to be used for constructing gels in situ, in 3D printing or in an organism, for example, if a corresponding composition is injected.

In one preferred embodiment the conditions are selected such that gelling is achieved within from 3 seconds to 5 minutes. The gelling time here may be adjusted preferably by way of the macromer concentration, pH, and temperature. This also permits adjustment to the physical properties of the gels, such as long-term stability, swelling behavior, and mechanical properties.

The reaction is also orthogonal to OH groups, amino groups, carboxylic acid groups and acrylate groups which do not react under physiological conditions.

In one preferred embodiment of the invention the reaction of the two macromers contributes exclusively to the formation of the hydrogel. No other crosslinking reactions take place.

The rate of the reaction may be controlled through the choice of the aromatic or heteroaromatic group which carries the sulfonyl group, and by the choice of pH. The gelling rate can be adapted accordingly to the particular use. In contrast to other reactions, there is no need to add any initiator or accelerator.

The ratio of the two macromers is preferably selected such that, after the reaction, all of the functional groups have reacted. The ratio may depend on whether further functionalizations are carried out.

It is thus possible, for example, to modify the second macromer by prior addition of thiol-containing compounds, before initiating the crosslinking and formation of the hydrogel by adding the first macromer. In this way the hydrogel may be modified with further functions. Fluorophores or bioactive reagents, for example, are possible.

Examples of bioactive reagents are tissue growth promoters, chemotherapeutic agents, proteins (glycoproteins, collagen, lipoproteins), cell binding mediators, for example fibronectin, laminin, collagen, fibrin, or integrin-binding sequences (for example cyclo(RGDfC) or cadherin-binding sequences, growth factors, differentiation factors or fragments of the aforesaid reagents. Examples are epidermal growth factor EGF, endothelial growth factor VEGF, fibroblast growth factors such as bFGF, insulin-like growth factors (e.g., IGF-I, IGF-II), transforming growth factors (e.g., TGF-α, TGF-β), DNA fragments, RNA fragments, aptamers or peptidomimetics; preference is given to cell-binding mediators such as VEGF.

The modification may be utilized, for example, in order to create appropriate environments in the hydrogel depending on the cells to be cultivated.

The reagents are used preferably in effective concentrations—this may be, for example, in the range from 0.01 to 100 mM, preferably 0.1 mM to 50 mM, more particularly 0.2 mM to 10 mM, more particularly 0.5 to 5 mM, based on the swollen gel.

The invention also relates to a composition for producing a hybrid gel, comprising at least two macromers a1) and a2) as described for the process.

The invention also relates to a hydrogel obtained with the process of the invention.

The invention also relates to a hydrogel comprising a first multiplicity of macromers, which is crosslinked with a second multiplicity of macromers, where the crosslinking takes place via a multiplicity of Ar—S bonds, where Ar is an aromatic or heteroaromatic group.

A bond of this kind may be obtained as described above from the nucleophilic substitution by thiols on electron-deficient aromatics. Advantageous embodiments are described for the process.

The hydrogels of the invention have a long-term stability, preferably of up to 6 weeks. They can be obtained and modified in a simple way and under physiological conditions.

They are especially suitable for encapsulating cells, for three-dimensional cell cultures, organoids, biomaterials, injectable biomaterials, cell therapies, tissue modification, tissue regeneration, tissue transplantation, regenerative medicine, 3D printing, 3D bioprinting, wound dressings or wound treatment, transport agents for active ingredients, in vitro models for studying or testing diagnostic or therapeutic agents, or cell transplantations.

Because of the reaction under physiological conditions, the stated reaction can be employed in particular in the biological sector. It is conceivable, for example, for the two macromers reacting with one another to be mixed or combined with one another only in situ. This may be accomplished, for example, by means of a multicomponent syringe.

The invention relates to a process for enveloping cells, where the hydrogel is formed in the presence of the cells in order to envelope the cells. This may be used, for example, for cell culture, more particularly for three-dimensional cell culture.

The invention also relates to a kit for producing a hydrogel, comprising the macromers a1) and a2) as described for the process.

The reaction described is also suitable for accomplishing additional crosslinking of existing gels. In a process of this kind, a gel comprising at least two of the functional groups of component a1) or a2), as known, for example, from A. Farrukh, J. I. Paez, M. Salierno, A. del Campo, *Angew. Chem. Int. Ed.* 2016, 55, 2092-2096 by copolymerization of such monomers into polyacrylamide gels, is provided and is reacted with a macromer having corresponding functional groups in accordance with macromer a1) or a2), where in this case the macromers a1) or a2) contain at least two of the functional groups, so that the gel is crosslinked as a result of this reaction.

The invention therefore also relates to a process for modifying gels, comprising the steps of:

a) providing a gel or a precursor thereof, comprising at least two functional groups as per component a1) or at least two functional groups as per component a2);
b) adding a composition comprising at least one macromer as per the respectively other component, where the macromer contains at least two functional groups;
c) modifying the gel or the precursor thereof by reacting the functional groups.

The process is preferably used after the preparation of the gel, for retrospective modification. As a result it is possible to modify the gel under physiological conditions in order to adapt its mechanical parameters, for example.

Because of the pH dependence and/or temperature of the reaction, it is possible, for example, for this modification to occur only in the case of a defined change in the conditions.

Further details and features are apparent from the description hereinafter of preferred working examples in conjunction with the dependent claims. In this context the respective features may be actualized on their own or multiply in combination with one another. The possibilities for achieving the object are not confined to the working examples. For instance, range indications always encompass all—unstated—intermediate values and all conceivable subintervals.

BRIEF DESCRIPTION OF THE DRAWINGS

The working examples are represented in the figures. In the examples the macromers are referred to as polymers.

DETAILED DESCRIPTION OF INVENTION

Figure 1:
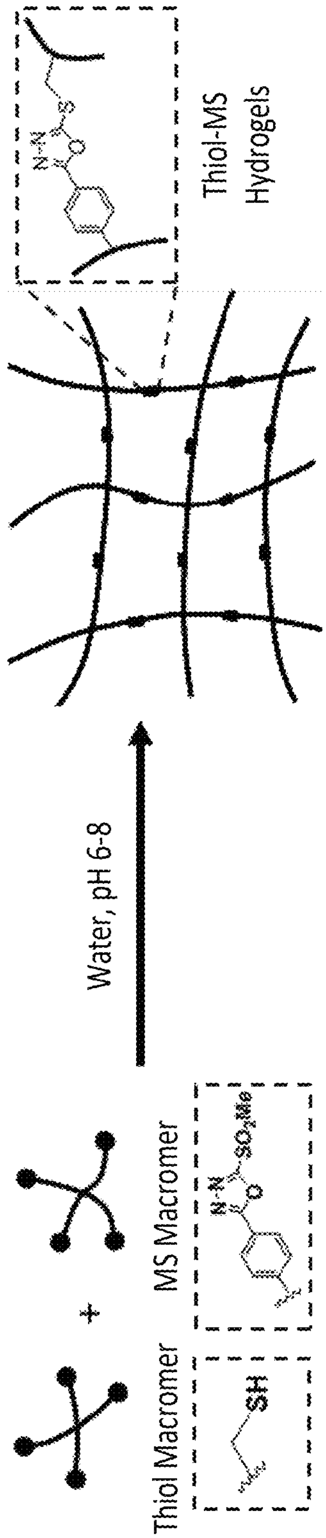
FIG. 1 Schematic representation of the preparation of a hydrogel in accordance with the invention.

Chemical and solvents were acquired in p.a. purity and used directly unless otherwise described. 4-(5-Methylsulfonyl)-1,3,4-oxadiazol-2-yl)aniline was acquired from Ark Pharm USA. 4-Armed polyethylene glycol polymers (PEG, 20 kDa on the basis of pentaerythritol) functionalized with maleimide (PEG-Mal), vinyl sulfone (PEG-VS), thiol (PEG-SH) and N-succinimidyl carboxymethyl ester (NHS-PEG) and linear methoxylated PEG polymer (5 kDa) also functionalized in each case with NHS, SH, Mal and VS were acquired from Jenkem, USA. Buffer solutions were prepared freshly. 10 mM HEPES (pH 8.0, 7.0, and 6.7) and phosphate-buffered saline solution (PBS, pH 7.4 and 7.0) were used.

Deuterated solvents were obtained from Deutero GmbH Deutschland (D-56288 Kastellaun). Deuterated phosphate buffer saline solution (PBS) was prepared by dissolving the correct amount of disodium phosphate, monosodium phosphate, sodium chloride and potassium chloride in $D_2O$; followed by a pD adjustment with 20% DCl solution (Merck), until the pD values of 8.0, 7.4, 7.0, 7.0 and 6.0 were reached. The pH was monitored using pH meters and the following correction factor was applied: $pD=pH_{obs}+0.4$ (see Bates et al., Anal. Chemie 1968 40 (4), 700-706).

Thin-layer chromatography (TLC) plates (ALUGRAM® SIL G/UV254) and silica gel for column chromatography (60 Å pore size, 63-200 μm particle size) were obtained from Macherey-Nagel, (52355 Duren) Germany. TLC plates were observed under 254 or 365 nm light. HPLC analysis and HPLC purification of the compounds were carried out using an HPLC JASCO 4000 (Japan) equipped with a diode array, UV-Vis detector and fraction collector. Reprosil C18 columns were used for semipreparative (250×25 mm) and analytical (250×5 nm) runs. Solvent gradients were used with a combination of the following eluents: solvent A (MilliQ water+0.1% TFA) and solvent B (95% ACN/5% MilliQ water+0.1 TFA), typically over 40 minutes. Modified polymers were purified typically by dialysis against acetone and water. Spectra/Por 3 dialysis tubes (molecular weight cutoff limit MWCO=3.5 kDa) from Spectrum Inc. were employed.

The $^1H$-NMR and $^{13}C$-NMR solution spectra were recorded at 25° C. on a Bruker Avance 300 MHz or on a Bruker Avance III UltraShield 500 MHz. The latter was equipped with an He-cooled 5 mm TCI CryoProbe, a proton-optimized triple-resonance NMR inverse probe with external water cooling (CP TCI 500S2, H-C/N-D-05 Z). Unless otherwise indicated, all measurements were conducted at 298K. Tetramethylsilane (TMS) (δ=0 ppm) was used as internal reference. The chemical shifts are reported in parts ppm and the coupling constants in hertz. Abbreviations used are as follows: s-singlet, d-doublet, t-triplet, q-quartet, m-multiplet. The degree of substitution of the PEG polymer was calculated by end group determination. The integral of the signal corresponding to the PEG backbone (3.70-3.40 ppm) was set at 440H and compared with the integral of the protons corresponding to the incorporated molecule 2 (the aromatic —CHs at 8.10-7.70 ppm and the methylene at 4.20 ppm). Degrees of functionalization of >91% and yields of >91% were achieved in all cases. The data were analyzed in MestReNova.

Mass spectra were recorded using Agilent Technologies 1260 Infinity Liquid Chromatography/Mass. Selective detector (LC/MSD) and 6545 accurate-mass quadrupole time of flight (LC/Q-TOF-MS) using chemical ionization by electrospray. UV/VIS spectra were recorded using a Varian Cary 4000 UV/VIS spectrometer (Varian Inc. Palo Alto, USA).

The rheological properties of hydrogels were determined on a discovery HR-3 rheometer (TA Instruments, USA), equipped with 12 mm parallel plates and Peltier platform, at 25 and 37° C. The software was Trios v4. Data were recorded and analyzed in Origin 9.1.

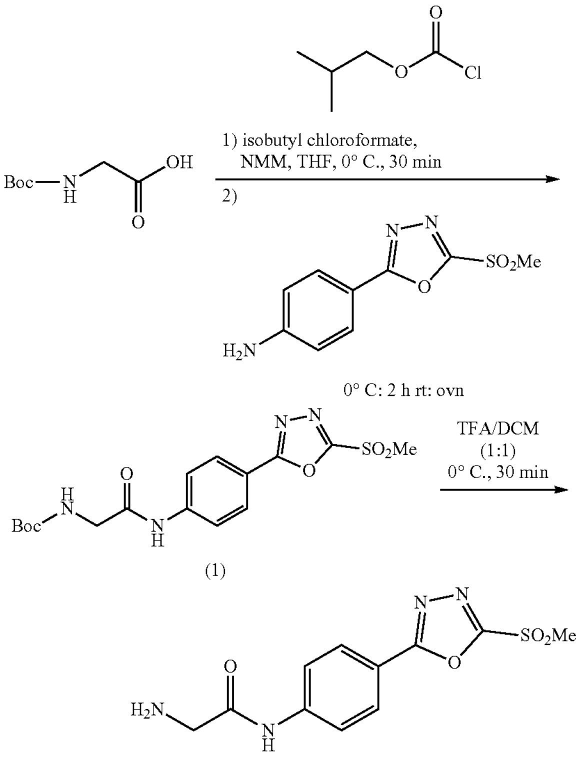

(1)

(2)

The following protocols were adopted with certain modifications: G. Liang et al., *Chem. Commun.*, 2017, 53, 3567-3570; J. Ling et al., *Chem Bio Chem* 2018, 19, 1060.

Synthesis of tert-butyl (2-((4-(5-(methylsulfonyl)-1,3,4-oxadiazol-2-yl)phenyl)amino)-2-oxoethyl)carbamate (1)

Boc-Gly-OH (1 eq, 2.28 mmol), 0.394 g) was dissolved in anhydrous THF (3 ml) at 0° C. Isobutyl chloroformate (1.2 eq, 2.85 mmol, 0.314 ml) and N-methylmorpholine (2.6 eq, 5.7 mmol, 0.627 ml) were added to the solution carefully with a syringe under a nitrogen atmosphere, followed by stirring for 30 minutes. A solution of 4-(5-(methylsulfonyl)-1,3,4-oxadiazol-2-yl)aniline (0.25 eq, 0.57 mmol, 0.136 g) in THF (3 ml) was added dropwise to the mixture, followed by stirring at 0° C. for 2 h more and then at room temperature overnight. Saturated $NaHCO_3$ was added and the reaction mixture was extracted with ethyl acetate (2×30 ml). The combined organic phase was dried over sodium sulfate, filtered, evaporated, and purified by preparative HPLC (5B to 95B 280 nm, reaction time=28 min), and a white solid was obtained after freeze-drying, 165 mg (yield=73%).

Synthesis of 2-amino-N-(4-(5-(5-(methylsulfonyl)-1,3,4-oxadiazol-2-yl)phenyl)acetamide (2)

Compound 1 (45 mg) was dissolved in 1:1 TFA/DCM (2 ml) and the solution was stirred at room temperature for 2 h and evaporated under a stream of nitrogen. The end product was obtained after HPLC purification (5B to 95B 280 nm, reaction time=18 min) (Y=>99%). The pure compound was immediately coupled to the PEG polymer, since otherwise decomposition was observed over the course of 1 week after storage at −20° C.

Synthesis of PEG-MS:

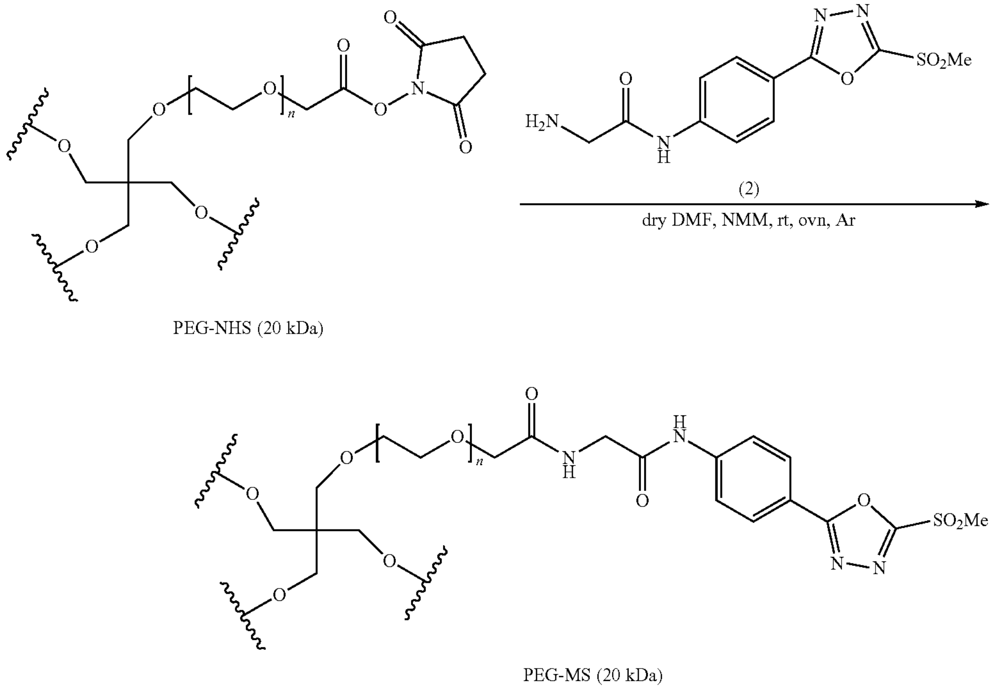

(2)

PEG-NHS (20 kDa)

PEG-MS (20 kDa)

The freshly prepared compound 2 (50 μmol, 15 mg) and N-methylmorpholine (18 μmol, 20 μL) were dissolved in dried DMF (2 ml), flushed with nitrogen and stirred for 15 min. 20 kDa, 4-armed PEG-NHS (100 mg, 5 μmol) were dissolved in dry DMF (1 ml) and added under a stream of nitrogen. The mixture was stirred at room temperature overnight under an inert atmosphere, then dialyzed in acetone and water and freeze-dried. A solid white polymer was obtained and was characterized by means of $^1$H-NMR in DCM-$d_2$. A degree of functionalization of >91% and a yield of >90% were calculated.

The 2-(methylsulfonyl)-5-phenyl-1,3,4-oxadiazole group was selected as MS substrate for the thiol coupling. Under the heteroaromatic MS rings described, this substrate reacts with thiols with a high conversion and moderate reaction rate [N. Toda, S. Asano, C. F. Barbas, *Angew. Chem., Int. Ed.* 2013, 52, 12592-12596, X. Chen, H. Wu, C.-M. Park, T. H. Poole, G. Keceli, N. O. Devarie-Baez, A. W. Tsang, W. T. Lowther, L. B. Poole, S. B. King, M. Xian, C. M. Furdui, *ACS Chemical Biology* 2017, 12, 2201-2208]. 4-Armed PEG-MS macromers (20 kDa) were synthesized on the 500 mg scale in a good yield (degree of substitution >91%) over the course of three synthesis steps.

Rheological Measurements on Hydrogels

Figure 2:
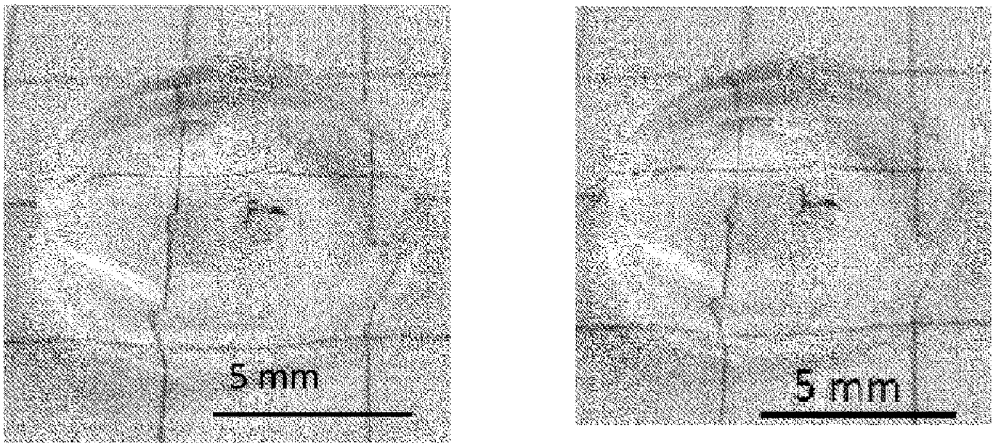
FIG. 2 a) photo of a PEG-thiol-MS hydrogel (5 wt % polymer concentration in 10 mM HEPES buffer); b) shear moduli during the gelling (5 wt % polymer, 10 mM HEPES buffer pH 6.6, T=25° C.)
Figure 2:
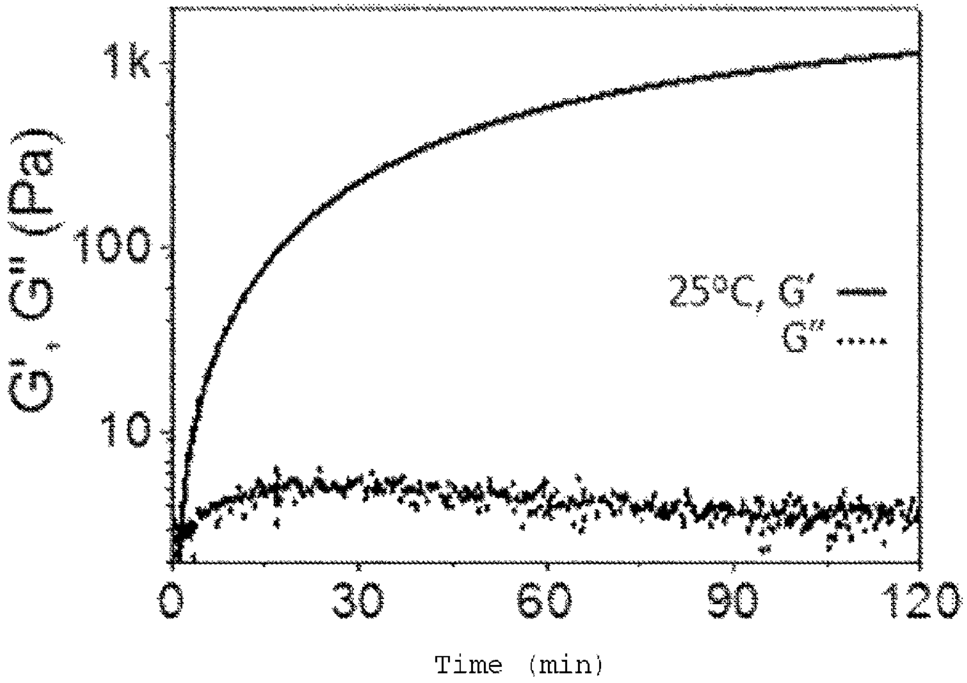

The gelling of the 4-arm PEG-MS and 4-arm PEG-thiol mixture was studied. Crosslinking conditions employed were 5 wt % polymer content in 10 mM HEPES buffer, pH 6.6, at 25° C. An MS:thiol ratio of 1:1 was used for the experiments. Studies showed that thiol-MS gels formed a crosslinked gel within 3-4 min (see table 1). This corresponds to a favorable crosslinking time, enabling flawless mixing and homogenization of precursor solutions. Rheological studies revealed that the crosslinked gels attain a shear storage modulus of G'~1 kPa (FIG. 2*b*). A swollen PEG-thiol-MS hydrogel (5 wt % polymer concentration in 10 mM HEPES buffer) is shown in FIG. 2*a*.

20 kDa, 4-armed PEG-X polymer solutions were freshly prepared and used for these studies. The polymer was dissolved in the corresponding solvent, mixed by means of a vortexer, held in an ultrasound bath and centrifuged in order to remove bubbles. 21 μL of a 5% w/v PEG X solution were applied to the lower Peltier plate of the rheometer, followed by 21 μL of a 5% w/v PEG-thiol solution, with mixing taking place with the tip of the pipette directly on the plate. The upper plate was brought nearer, in order to place the sample between the two plates, and the sample was subsequently sealed with liquid paraffin in order to prevent evaporation during the measurement. The overall sample loading time including the start of the measurement was around 2-3 min.

The gelling time and the final shear modulus of the hydrogel were determined rheometrically. Strain runs (0.1 to 1000% strain at frequency=1 Hz) and frequency runs (0.01 to 100 Hz at strain=1%) were carried out in order to determine the linear, viscoelastic regime. The time runs were carried out within the linear viscoelastic regime, with the following parameters: slot 300 μm, axial force (0.0±0.1 N), frequency 1 Hz, strain 1%, temperature=25 or 37° C.

Hydrogels were prepared at 5 wt % polymer content, HEPES buffer pH 8.0 and T=25° C. (FIG. 3*a*) and T–37° C. (FIG. 3*b*).

Figure 3A:
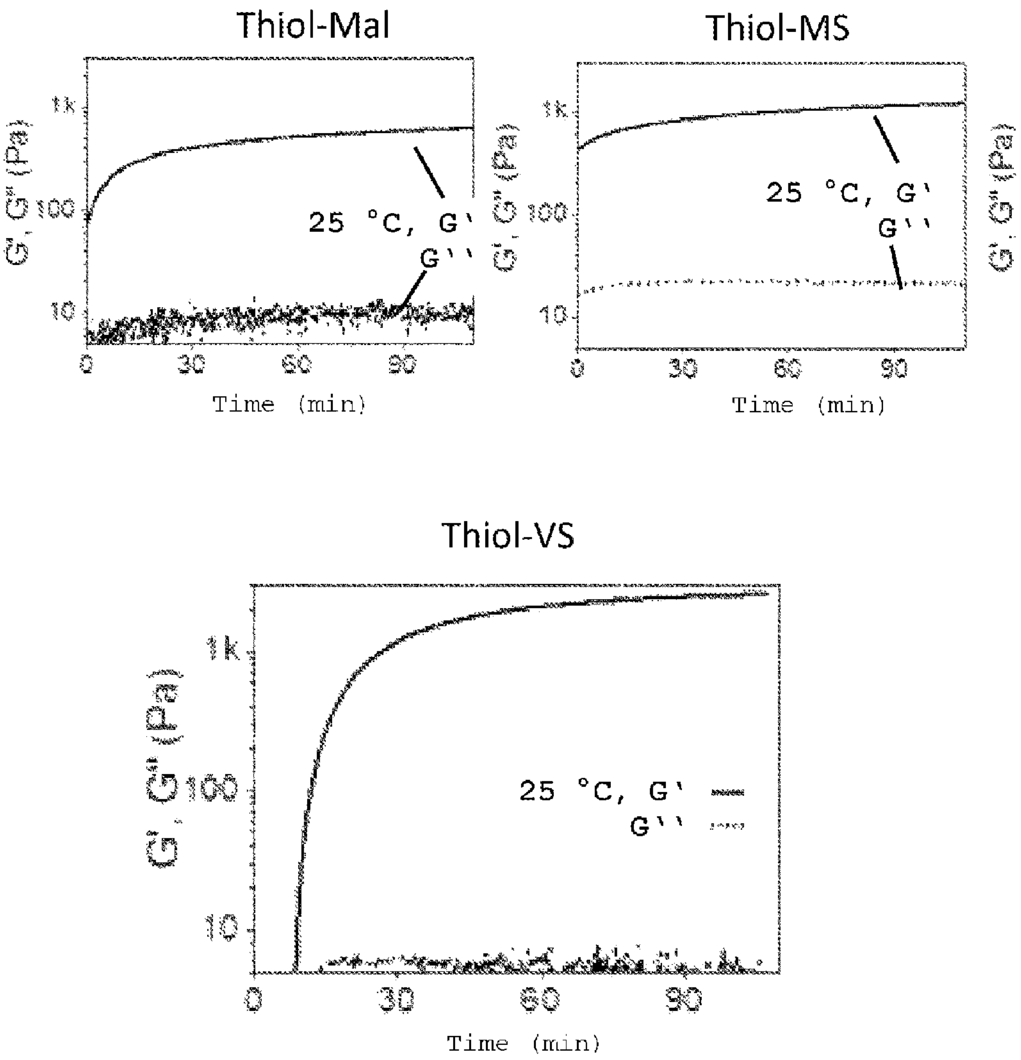
FIG. 3*a* shear moduli during the gelling of the various hydrogels at 25° C. (in each case 5 wt %; 10 mM HEPES buffer; pH 8)
Figure 3B:
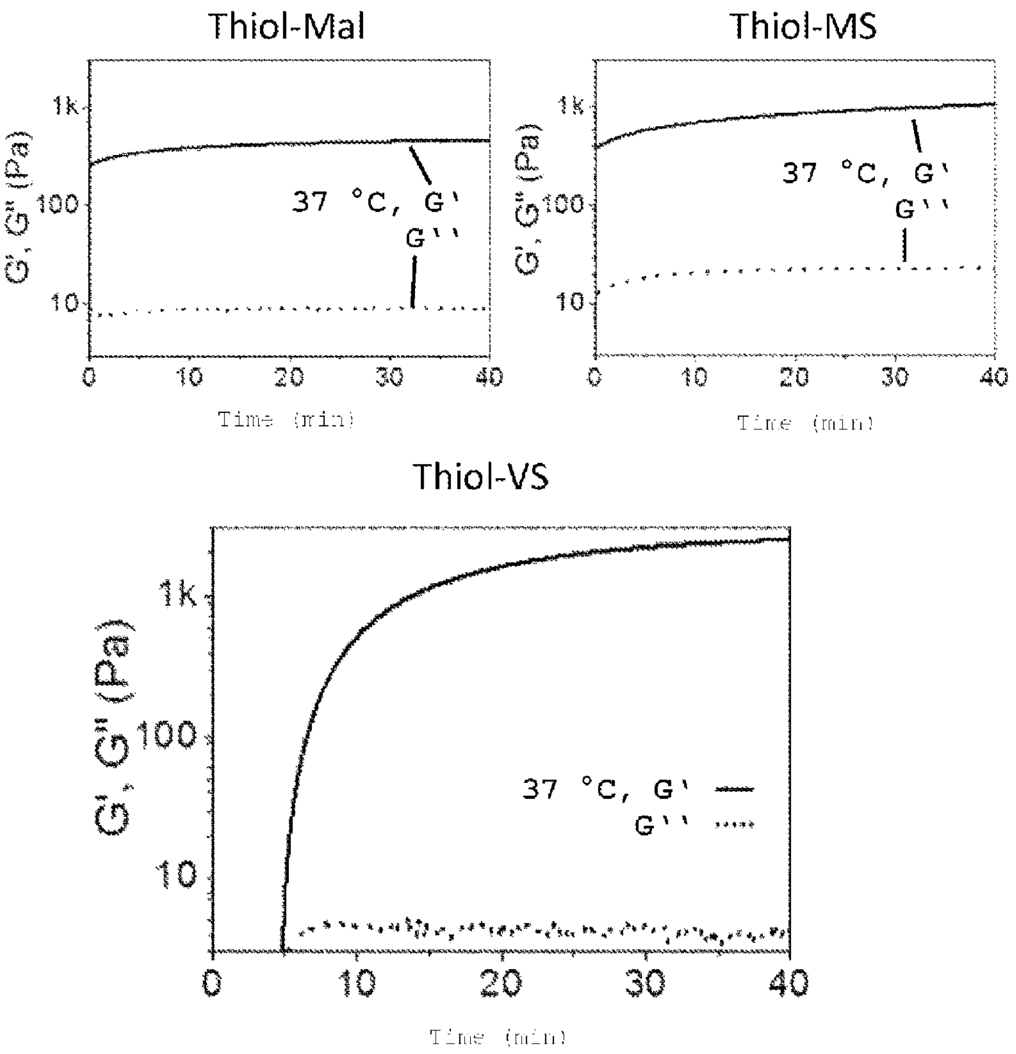
FIG. 3*b* shear moduli during the gelling of the various hydrogels at 37° C. (in each case 5 wt %; 10 mM HEPES buffer; pH 8) FIG. 4 effect of pH (at 5 wt % polymer content, 25° C.) on the crosslinking kinetics and the shear moduli (a) thiol-Mal, thiol-MS, b) thiol-VS)

FIG. 3*a* compares the crosslinking kinetics of thiol-MS with that of thiol-Mal and thiol-VS systems. The experiments were conducted under conditions typical of cell culture (5 wt % polymer, in 10 mM HEPES buffer pH 8.0, at 25° C.) [E. A. Phelps, N. O. Enemchuwu, V. F. Fiore, J. C. Sy, N. Murthy, T. A. Sulchek, T. H. Barker, A. J. Garcia, *Advanced Materials* 2012, 24, 64-70. A. Farrukh, J. I. Paez, A. del Campo, *Advanced Functional Materials* 2019, 29, 1807734]. Under these conditions the thiol-MS gel was formed in 3-4 s (table 1). This corresponds to a short crosslinking time, but is acceptable for the mixing and homogenizing of gel precursors. In comparison to this, the thiol-Mal gel took 1 s for crosslinking and the resulting gels were nonuniform, while the thiol-VS system gave a gelling time of around 10 min and took around 2 h in order to complete the crosslinking. These results show the following trend in the gelling rate: thiol-Mal>thiol-MS>thiol-VS, in agreement with the specified reaction rates for model compounds [X. Chen, H. Wu, C.-M. Park, T. H. Poole, G. Keceli, N. O. Devarie-Baez, A. W. Tsang, W. T. Lowther, L. B. Poole, S. B. King, M. Xian, C. M. Furdui, *ACS Chemical Biology* 2017, 12, 2201-2208. F. Saito, H. Noda, J. W. Bode, *ACS Chemical Biology* 2015, 10, 1026-1033. H. Wang, F. Cheng, M. Li, W. Peng, J. Qu, *Langmuir* 2015, 31, 3413-3421], as shown in table 2.

The values of the shear modulus of the crosslinked gels after 1 h were in each case $G'_{25°\ C.}$=2000 Pa for thiol-VS, 1000 Pa for thiol-MS and 470 Pa for thiol-Mal. The greater stiffness of thiol-MS gels is likely due to a greater uniformity of the system as a consequence of the slower gelling kinetics, leading to fewer network defects and to a higher degree of crosslinking.

This result contradicts earlier reactivity studies of thiol-Mal and thiol-MS couplings on small model molecules, which showed similar conversions in phosphate buffer saline solution (PBS) pH 7.4 [N. Toda, S. Asano, C. F. Barbas, *Angew. Chem., Int. Ed.* 2013, 52, 12592-12596]. We assumed that the hydrolysis of Mal groups, which occurs at basic pH, might be the reason for the lower mechanical properties of thiol-Mal. In order to verify this hypothesis, the stability of a 4 wt % PEG-Mal solution in deuterated PBS at pD 8.0 was studied by $^1$H-NMR.

The hydrolysis of Mal groups was detected after 2 hours. It is therefore not expected that the hydrolysis of Mal groups significantly influences the mechanical properties of thiol-Mal within the range of the conditions tested. Thiol-VS attained the highest shear modulus; this coincides with a higher conversion or with the slowest curing, which ensure a network with far fewer defects. All in all these results show that the thiol-MS crosslinking constitutes intermediate kinetics between the very rapidly crosslinking thiol-Mal and the slow thiol-VS-based materials. The crosslinking time observed, in the region of a few seconds, enables convenient mixing and pipetting of the components with low shearing forces, and appears suitable for cell encapsulation.

pH Dependence

The gelling of the 4-arm PEG-MS and 4-arm PEG-thiol mixture was studied (FIG. 1). Crosslinking conditions employed were 5 wt % polymer content in 10 mM HEPES buffer, pH 6.6, at 25° C. An MS:thiol ratio of 1:1 was used for the experiments. The gelling time in bulk for the thiol-X hydrogels was determined at different pH values. The experiments were conducted at 5 wt % polymer solution, in 10 mM HEPES buffer, T=25° C. The gelling time was estimated as the interval between the mixing of the components and the time at which it was no longer possible to carry out pipetting to the mixture. Studies showed that thiol-MS gels formed a crosslinked gel within 3-4 min (see table 1). This corresponds to a favorable crosslinking time, which permits faultless mixing and homogenization of precursor solutions.

Figure 4:
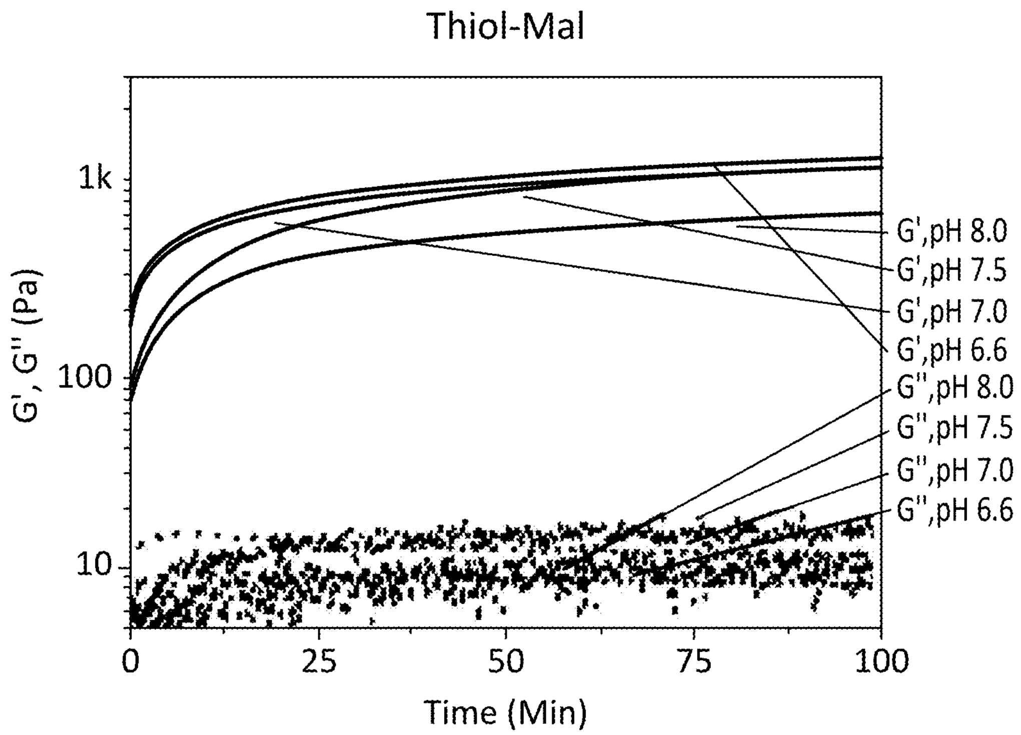
Figure 4:
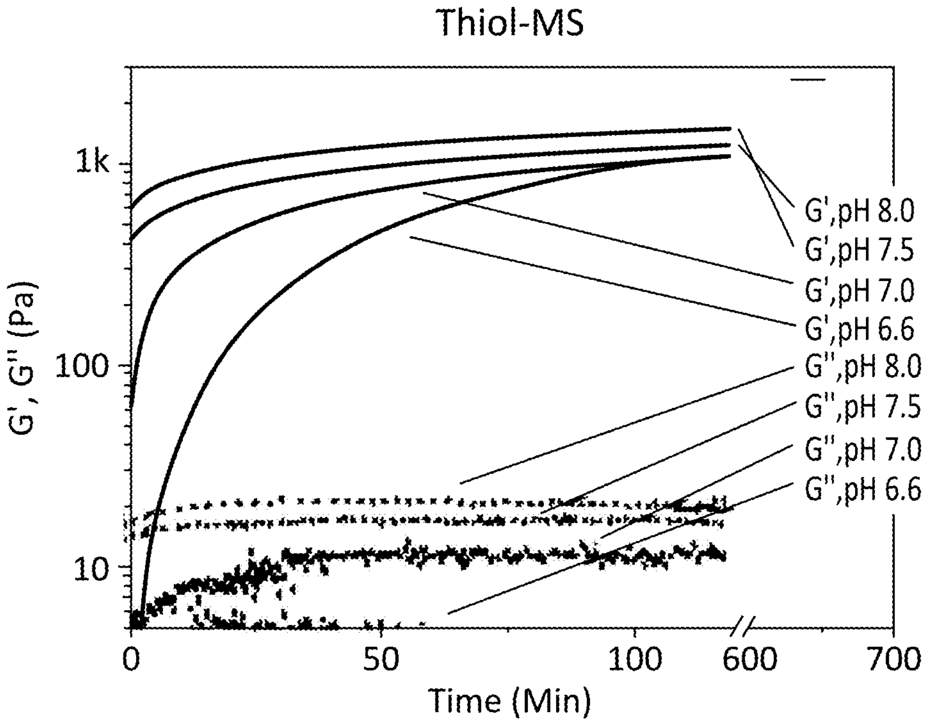
Figure 4:
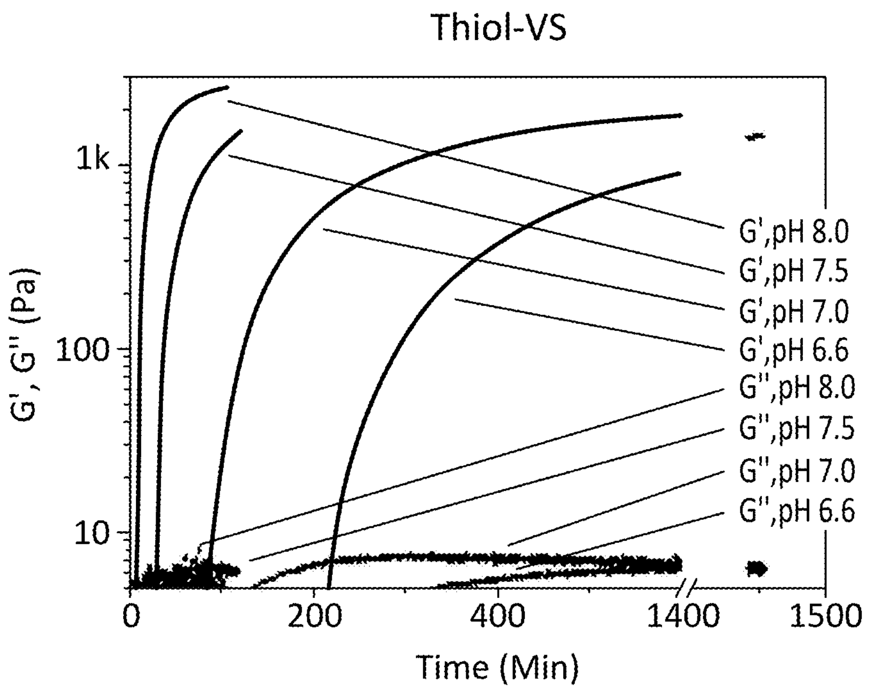

The reaction rate of the polar thiol-X coupling is dependent on the pH in the pH range between 6 and 9. This is due to the deprotonation of the thiol group (pKa~8) to the thiolate anion, which in these reactions acts as the nucleophile [M. H. Stenzel, *ACS Macro Letters* 2013, 2, 14-18]. This feature offers an interesting opportunity for pH-controlled curing kinetics under physiologically relevant conditions. The thiol-MS crosslinking was analyzed in the pH range of 8.0-6.6. A decrease in the crosslinking rate was observed with decreasing pH (FIGS. 4*a* and 4*b* and table 1). It is noteworthy that the pH change from 8.0 to 6.6 allowed the gelling time to be tailored from several seconds to a couple of minutes (table 1), which offers an ideal experimental time window for 3D cell encapsulation applications. In contrast to this, the gelling time of thiol-Mal varied only within a few seconds, while thiol-VS was situated between a few minutes and a few hours. These results illustrate the advantages of thiol-MS gels in terms of handling and adaptability to the application requirements, relative to thiol-Mal and thiol-VS.

The shear modulus of thiol-MS-crosslinked hydrogels was slightly influenced by the pH: at a pH of 8.0, they exhibited a relatively low G', probably because of the occurrence of the very rapid crosslinking, which led to a number of inhomogeneities and defects in the network. This was not the case with thiol-MS gels, which were formed at pH 7.5-6.6, in which similar ultimate G's were obtained. This therefore appears to be the optimum interval in which the crosslinking rate can be adjusted without detriment to the quality and mechanical stability of the gel. In comparison with this, the thiol-Mal system exhibited a fall in the mechanical properties at pH≥7.5, but a similar ultimate shear modulus at pH=7.0-6.6, while thiol-VS showed a clear trend to slower gelling kinetics and a slightly reduced shear modulus with decreasing pH. For this purpose, measurements were conducted in 10 mM HEPES buffer at pH values of 8.0, 7.5, 7.0 and 6.6, with 5 wt % polymer content and at 25° C. It is noteworthy here that the fastest-curing systems (Mal at pH≥7.0 and MS at pH≥7.5) cure instantaneously with loading of the rheometer (FIGS. 4*a* and 4*b*).

Influence of Temperature on Gelling Time 20 kDa, 4-armed PEG-X polymer solutions were freshly prepared and used for these studies. The polymer was dissolved in the corresponding solvent, mixed using a vortexer, held in an ultrasound bath, and centrifuged to remove bubbles. 30 μL of a 5% w/v PEG-X solution were placed into a plastic Eppendorf tube, followed by 30 μL of a 5% w/v PEG-thiol solution, with continuous mixing using the pipette. The gelling time “in the bulk” was recorded as the time in which the hardness mixture no longer flowed and continuous pipetting was not possible. The temperature was controlled using a water bath with temperature regulation.

Figure 5:
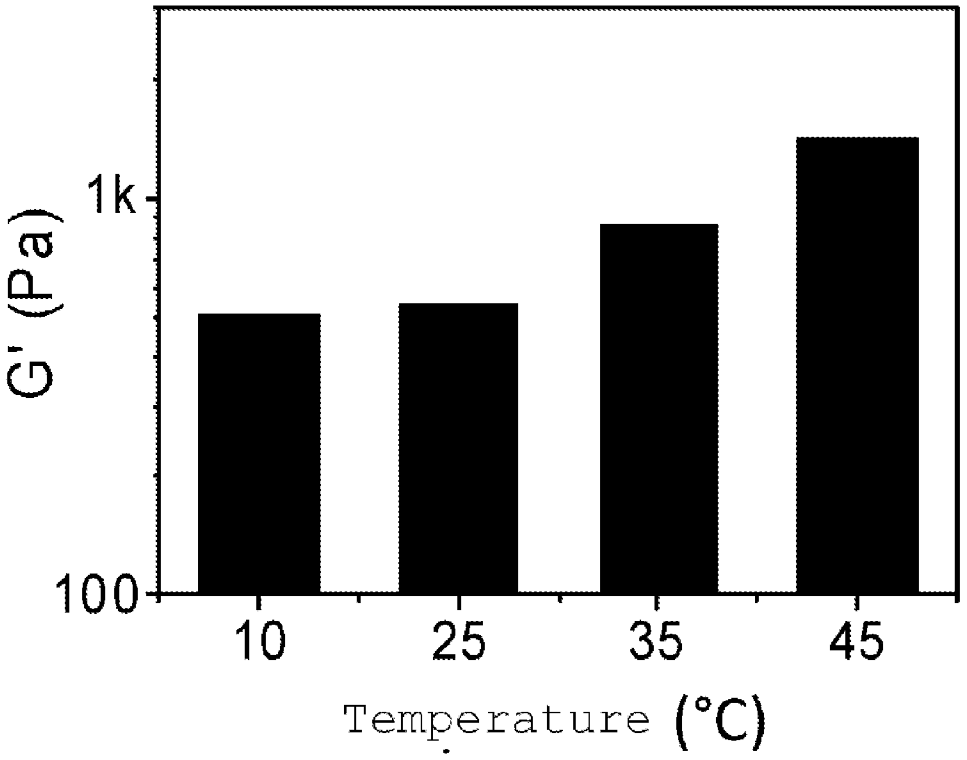
FIG. 5 shear modulus as a function of temperature (conditions: at 30 min, 5 wt %, pH 7.0)

The temperature can also be used for adjusting the thiol-MS gel properties. Lowering the temperature in the range from 45° C. to 25° C. enabled a decrease in the shear modulus (FIG. 5) and a prolongation of the gelling time (see table 3).

Influence of Polymer Content and HEPES Buffer Concentration on Thiol-MS Hydrogels Hydrogels were prepared with increasing polymer content values of 1.3, 2.5, 5.0, 7.5 and 10.0 wt %, at constant pH=7.5 and T=25° C., either with 10 mM or 50 mM HEPES buffer concentration. The pH of the hydrogels prepared was measured using a pH meter having a flat surface electrode (PH100 Waterproof ExStik® Extech Instruments, USA).

Lastly, a study was made of the influence of the polymer content on the thiol-MS hydrogel crosslinking kinetics and the shear modulus (FIG. 6*a*, 6*b*). The gelling time was shorter with increasing polymer content (in the range of 18-2 s; see table 4). Furthermore, G' rose with an increase in polymer concentration from 1.3 to 7.5 wt %, and fell at polymer concentrations above 10 wt %. This result was surprising, since precursor solutions could be correctly homogenized even at 10 wt %; therefore, there was no expectation that a poor mixing effect is responsible for this behavior.

Figure 6:
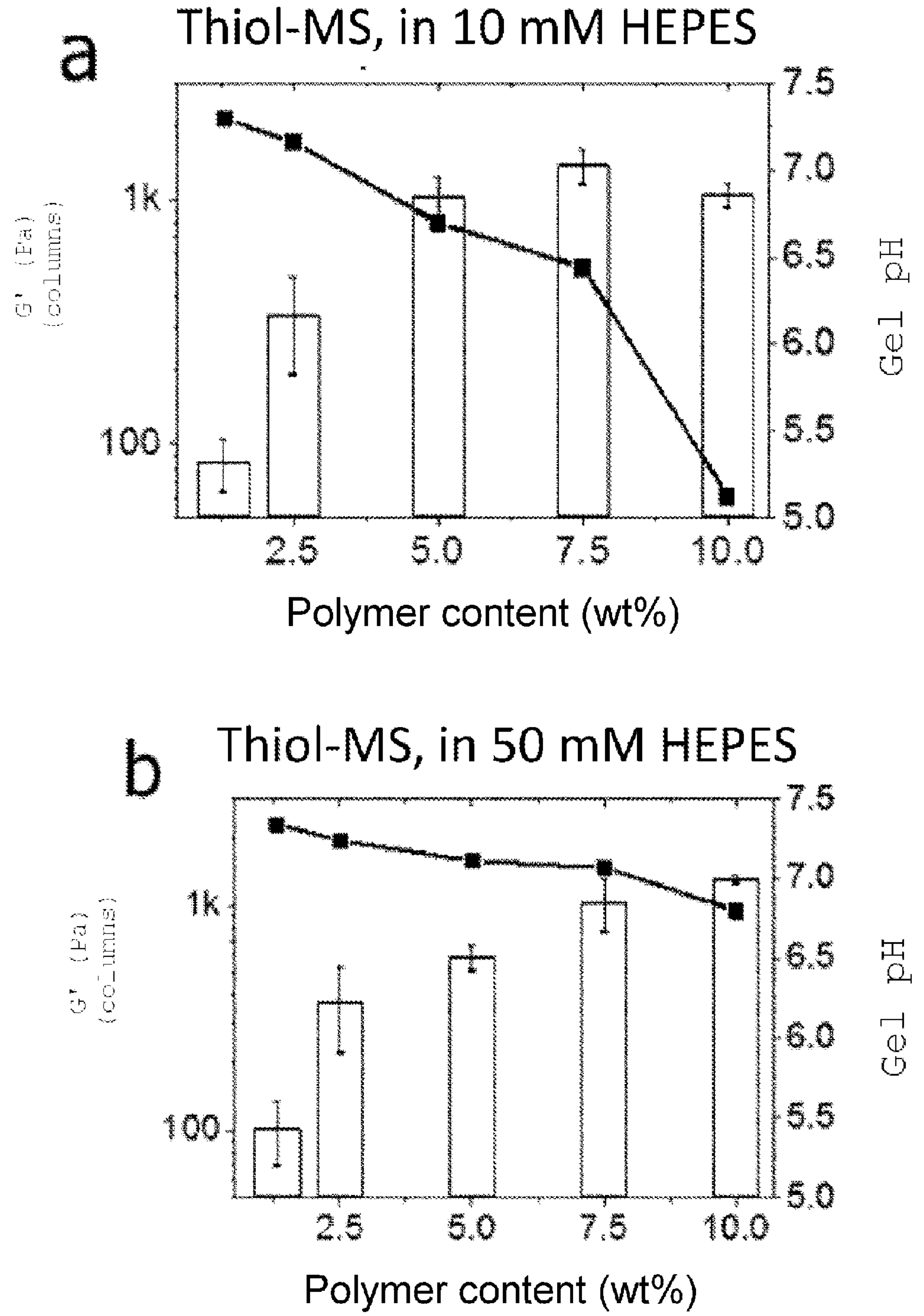
FIG. 6 influence of polymer content and HEPES buffer concentration on the mechanical properties (columns, left-hand scale) and pH (squares, right-hand scale) of the thiol-MS gels prepared. Conditions: pH=7.5, T=25° C., at 60 min.

In order to study the reaction mechanism, the pH of the resulting gels was measured (see FIG. 6*a*, 6*b*). It emerged that the pH of freshly prepared thiol-MS gels decreased as the polymer concentration increased. Gels between 1.3-7.5 wt % exhibited a pH between 7.5-6.5, while gels at 10 wt % had a pH in the vicinity of 5.1. This can be explained through the liberation of a methanesulfinic acid as leaving group in the thiol-MS coupling. With a high polymer fraction, the leaving group is produced in greater concentrations, leading to a reduction in pH of the crosslinking medium and hence to a reduction in the final shear modulus attained. This effect may be controlled by increasing the buffer capacity of the crosslinking medium, this being achieved by an increase in the HEPES buffer concentration from 10 mM to 50 mM (see FIG. 6). The latter concentration is known to still be cyto-compatible. These results show that the content of polymer can also be used to control the mechanical properties of the gel. At a relatively high concentration (10 wt %), the pH ought to be controlled by raising the buffer capacity.

Swelling Measurements on Thiol-X Hydrogels

These studies took place using precursor solutions of 5% w/v prepared in 10 mM HEPES buffer, pH 7.0, and cooled in an ice bath beforehand. 50 μL of a 5% w/v PEG-X solution were placed into a flexible PDMS cylinder mold (0.75 cm diameter), mixed rapidly with 50 μL of a 5% w/v PEG-Thiol solution, and crosslinked in a damp chamber at 37° C. for 4 h. The resulting hydrogels were carefully removed, swollen for 24 hours in Milli-Q water, and then subjected to determination of the mass of the swollen gel ($M_s$).

The gel was dried in an oven at 37° C. for 48 h and the mass of the dry hydrogel was ascertained ($M_d$). The swelling ratio (SR; degree of swelling) was calculated according to the following formula:

$$SR = \frac{M_s - M_d}{M_d}$$

The experiments were carried out three times. Mean values and standard deviations were reported.

The swelling ratio (SR) of 5% thiol-MS gels was measured in water at pH 7.0. Swelling of 33.6 mg water/mg polymer was obtained (see table 5). Thiol-VS gels show similar SR values, whereas thiol-Mal increased around 1.5 times more. These results indicate a similar degree of crosslinking of thiol-MS and thiol-VS networks and a lower crosslinking of thiol-Mal gels.

The hydrolytic stability is a relevant material property for hydrogels which are used in 3D cell culture.

Accordingly, the hydrolytic stability of 5 wt % thiol-MS gels was determined by gravimetric analysis of the swollen gel after incubation in the cell culture medium at 37° C. for different points in time over 4 weeks (FIG. 7*a*). In the first two weeks, the mass of the swollen thiol-MS gels reached 1.2 times the original mass, which suggests low gel erosion and high hydrolytic stability of the thiol-MS gels. It should be noted that the long-term stability of the gels is an advantage for long-term cell culture and enables the degradation properties to be finely tuned by copolymerization with specific degradable sequences [E. A. Phelps, N. O. Enemchukwu, V. F. Fiore, J. C. Sy, N. Murthy, T. A. Sulchek, T. H. Barker, A. J. Garcia, *Advanced Materials* 2012, 24, 64-70]. The stability of the thiol-MS system was similar to that of thiol-VS, which is used typically for long-term cultures [M. P. Lutolf, G. P. Raeber, A. H. Zisch, N. Tirelli, J. A. Hubbell, *Advanced Materials* 2003, 15, 888-892] and much higher than in the case of thiol-Mal gels (1.2 times in 2 days and hydrogel disintegration on day 18) [N. Boehnke, C. Cam, E. Bat, T. Segura, H. D. Maynard, *Biomacromolecules* 2015, 16, 2101-2108]. The hydrolysis of thiol-Mal gels is attributed to the low stability of the thioether-succinimide bond, which is able to pass through retro-Michael reactions and exchange reactions in the presence of other soluble thiols in cell culture media. The results agree with the studies using model-MS compounds, which show a superior stability of thio-heteroaromatic conjugates, which result from the thiol-MS coupling relative to thiol-Mal compounds under therapeutically relevant conditions [N. Toda, S. Asano, C. F. Barbas, *Angew. Chem., Int. Ed.* 2013, 52, 12592-12596]. Lastly experiments conducted with gels at 10 wt % showed that thiol-MS gels remained hydrolytically stable for more than 6 weeks (see FIG. 7*b*).

Use for Cell Encapsulation

PEG Hydrogel Preparation for 3D Cell Culture

3D PEG hydrogels were prepared by adaptation of the protocol described (Phelps et al., *Advanced Materials* 2012, 24, 64-70; and Farrukh et al., *Adv. Funct. Mater.* 2018). The precursor solution of 20 kDa 4-arm PEG Mal/VS/MS (100 mg $mL^{-1}$, 10% w/v) was prepared by dissolution in the HEPES buffer (10 mM, pH 8.0) in a sterile laminar flow. Solutions of cyclo (RGDfC) (3.45 mg $mL^{-1}$, 5 mM) and VPM peptide (GCRDVPMSMRGDRCG, 26.6 mg $mL^{-1}$, 15.68 mM) were prepared likewise in the sterile HEPES buffer (pH 8.0). These concentrations were kept constant during all of the cell experiments.

4-Arm PEG Mal/MS/VS stock solution (10% w/v) was mixed in a volume ratio of 2:1 with 5 mM cyclo(RGDfC) and incubated at 37° C. for 30 min. The cell suspension ($10\times10^{-6}$ cells/$mL^{-1}$) in RPMI medium (2 μL) was added to the above solution, and 8 μL drops of the resulting mixture were placed respectively into an Ibidi 15 μ-titer plate angiogenesis slide. The solution of VPM peptide (2 μL, 15.8 mM) was placed immediately into each μ-titer plate, carefully mixed using the pipette tip, and crosslinked. For 15 minutes the polymerization of the Mal and MS 3D hydrogels was carried out, while VS hydrogels were polymerized for 45 minutes at 37° C. and 5% $CO_2$. Following gelling, the RPMI medium was added and the culture was maintained for 1-3 days. Alternatively, for the spheroid culture, the RPMI medium (2 μL) was mixed with the cyclo(RGDfC)-modified PEG precursor solution (6 μL, as described above) and introduced respectively (8 μL) into the μ-titer plate. A fibrin clot was added to each titer plate, followed by the addition of 15.8 mM VPM peptide (2 μL), which was able to undergo gelling at 37° C. for 15-45 min. The medium was added to each titer plate and replaced by fresh medium every 24 hours during cell culture.

Figure 8:
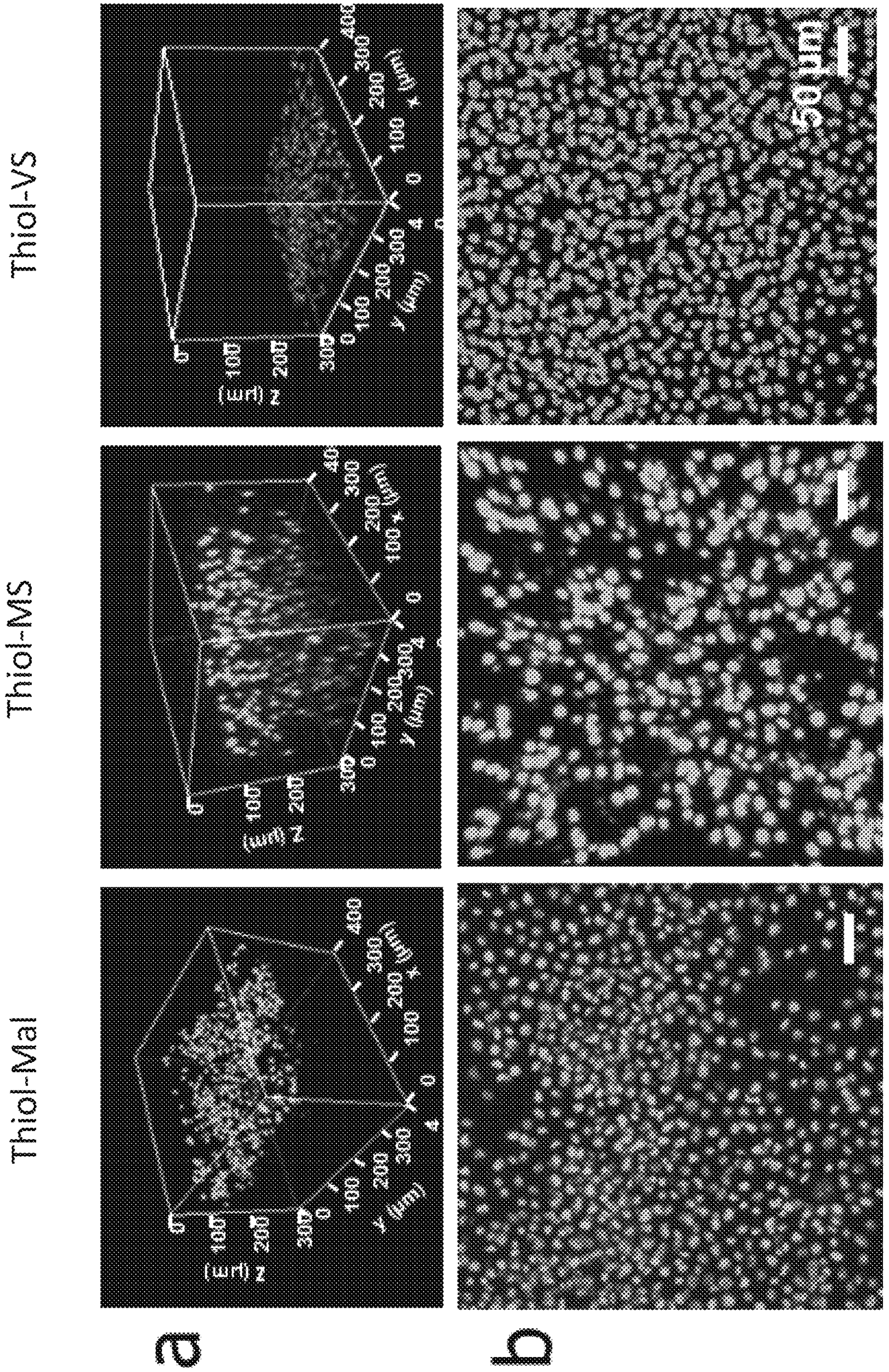
FIG. 8 Fibroblast L929 encapsulated in the various enzymatically cleavable thiol-X hydrogels. Living/dead assay of L929 fibroblast single cells encapsulated for 1 day in the materials (a-c): in comparison to the other systems, cells cultivated in thiol-MS hydrogels showed a more uniform distribution over the entire material (a, Z-stack) and a similar viability (c)
Figure 8:
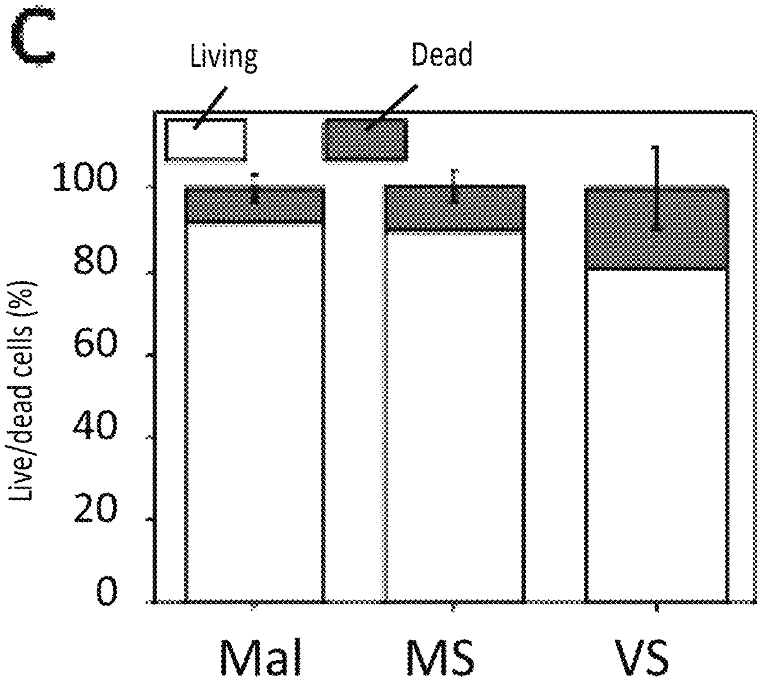

With this process, the PEG-MS component is initially functionalized with the cyclo(RGDfC) peptide, then mixed with L929 fibroblasts, and finally crosslinked with an enzymatically cleavable dithiol peptide (VPM). A composition of 4 wt % PEG-MS, 1 mM RGD peptide and 3.14 mM VPM was used [E. A. Phelps, N. O. Enemchukwu, V. F. Fiore, J. C. Sy, N. Murthy, T. A. Sulchek, T. H. Barker, A. J. Garcia, *Advanced Materials* 2012, 24, 64-70. A. Farrukh, J. I. Paez, A. del Campo, *Advanced Functional Materials* 2019, 29, 1807734]. After the mixing, the solution remained highly mobile, allowing the mixture to be homogenized by pipetting at low shearing forces. A stable gel formed within 15 min, visible to the naked eye. The distribution of the cells within the hydrogel was analyzed by means of Z-stack imaging on a confocal microscope. A uniform distribution of the cells over the thickness of the hydrogel was observed (FIG. 8*a*).

Cell Culture Conditions

The fibroblast L929 cell line (ATCC) was cultivated at 37° C. and 5% $CO_2$ in RPMI 1640 medium (Gibco, 61870-010), supplemented with 10% FBS (Gibco, 10270) and 1% P/S (Invitrogen). For suspended cell cultures, L929 cells ($10\times10^{6}$ cells $mL^{-1}$) were suspended directly in the PEG precursor solution during the polymerization.

For the spheroid culture, a fibrin clot of the fibroblast L929 cell line was prepared by means of the following literature reports (J. L. West, *Biomaterials* 2008, 29, 2962-2968; C. A. DeForest, K. S. Anseth, *Nature Chemistry* 2011, 3, 925-931).

In summary, a pellet of $10\times10^{6}$ cells $mL^{-1}$ was dissociated in fibrinogen (10 mg $mL^{-1}$ in PBS) and 2 μL drops were applied to a hydrophobic glass slide coated with Sigmacote. 1 μL of thrombin solution (5 UN $mL^{-1}$ in PBS) was added to each drop of fibrinogen, and the cells were placed into an incubator for 15 min in order to obtain a fibrin clot.

Fixing and Staining

3D PEG hydrogel samples were fixed using 4% PFA solution for 2 h at room temperature and washed with PBS. The samples were blocked with 1% BSA solution for 1 h, followed by permeabilization with 0.5% Triton X-100 for 1 h. FITC phalloidin (1:200 in water, Thermo Fisher Scientific) was used to stain actin fibers, and DAPI (1:500 in water, Life Technology) was used to stain nuclei. The samples were incubated with antibodies at RT for 5 h and subsequently washed with PBS.

Living-Dead Assay

The cell culture medium was removed and the samples were incubated for 5 min with fluorescein diacetate (40 μg $mL^{-1}$) and propidium iodide (30 μg $mL^{-1}$) in PBS. The samples were washed twice with PBS and recorded using the Zeiss LSM 880 confocal microscope.

Living/dead assays on cells encapsulated for 1 day in thiol-MS gels show the cytocompatibility of the material according to the invention (>90% viability, FIG. 8*a*, 8*b*, 8*c*). These results suggest that the crosslinking kinetics of the system are ideal to obtain uniform constructs under convenient and cytocompatible experimental conditions.

Conversely, thiol-Mal hydrogels resulted in immediate curing on mixing of precursor solutions, which made proper homogenization more difficult and resulted in cell agglomeration in the upper part of the gel. The thiol-VS system, for its part, enabled effective mixing, but the slow gelling kinetics resulted in cell sedimentation on the underside of the gel. These results are in agreement with earlier reports by Peyton et al. concerning the effect of the crosslinking rate in the context of the distribution of fluorescent beads encapsulated in thiol-Mal hydrogels [L. E. Jansen, L. J. Negrón-Piñeiro, S. Galarza, S. R. Peyton, *Acta Biomaterialia* 2018, 70, 120-128], and by Shikanov et al., which point to the need to turn thiol-VS gels during curing, in order to prevent cell depositions [J. Kim, Y. P. Kong, S. M. Niedzielski, R. K. Singh, A. J. Putnam, A. Shikanov, *Soft Matter* 2016, 12, 2076-2085]. In this context thiol-MS hydrogels exhibit more appropriate kinetics and overcome these inconveniences.

Migration Assay

Figure 7:
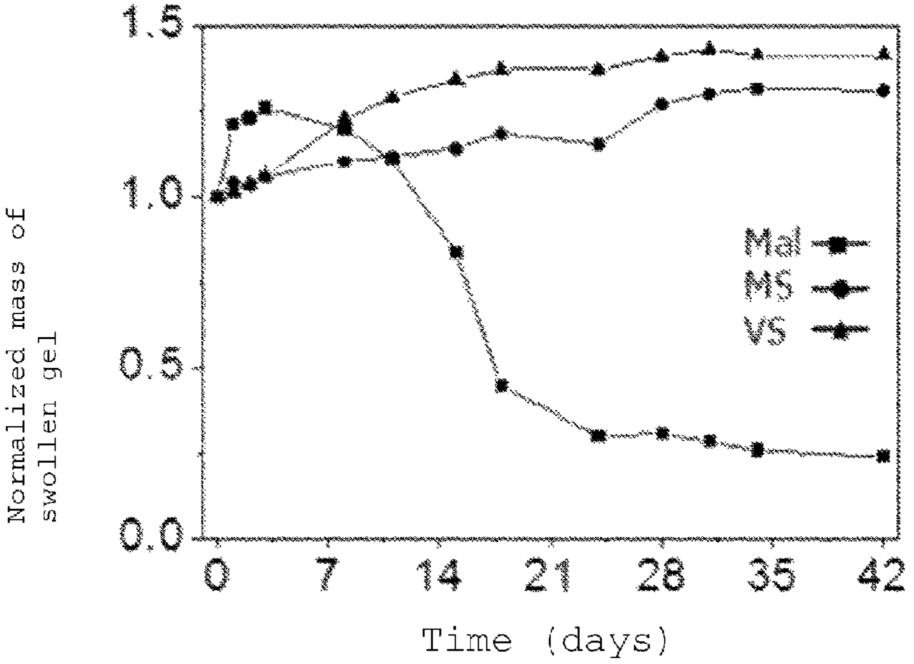
FIG. 7 comparison of the normalized mass of swollen thiol-X gels. Gels were incubated for 6 weeks or 4 weeks in the cell culture medium at 37° C. (a) 10 wt % polymer fraction, pH 8.0; b) 5 wt % polymer content at pH 7.0). Thiol-MS gels prepared under these conditions are stable to hydrolysis even after 6 weeks of incubation in the cell culture medium.
Figure 7:
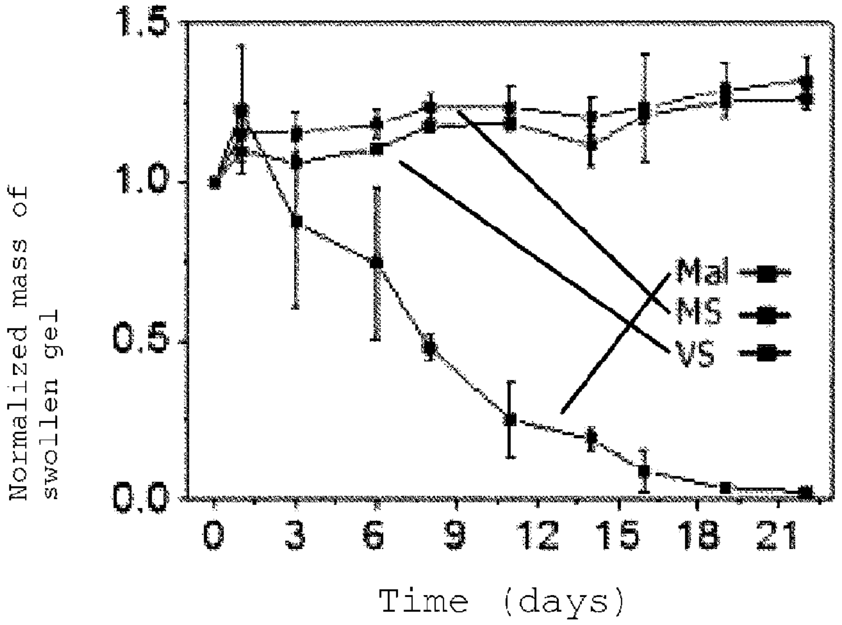
Figure 9:
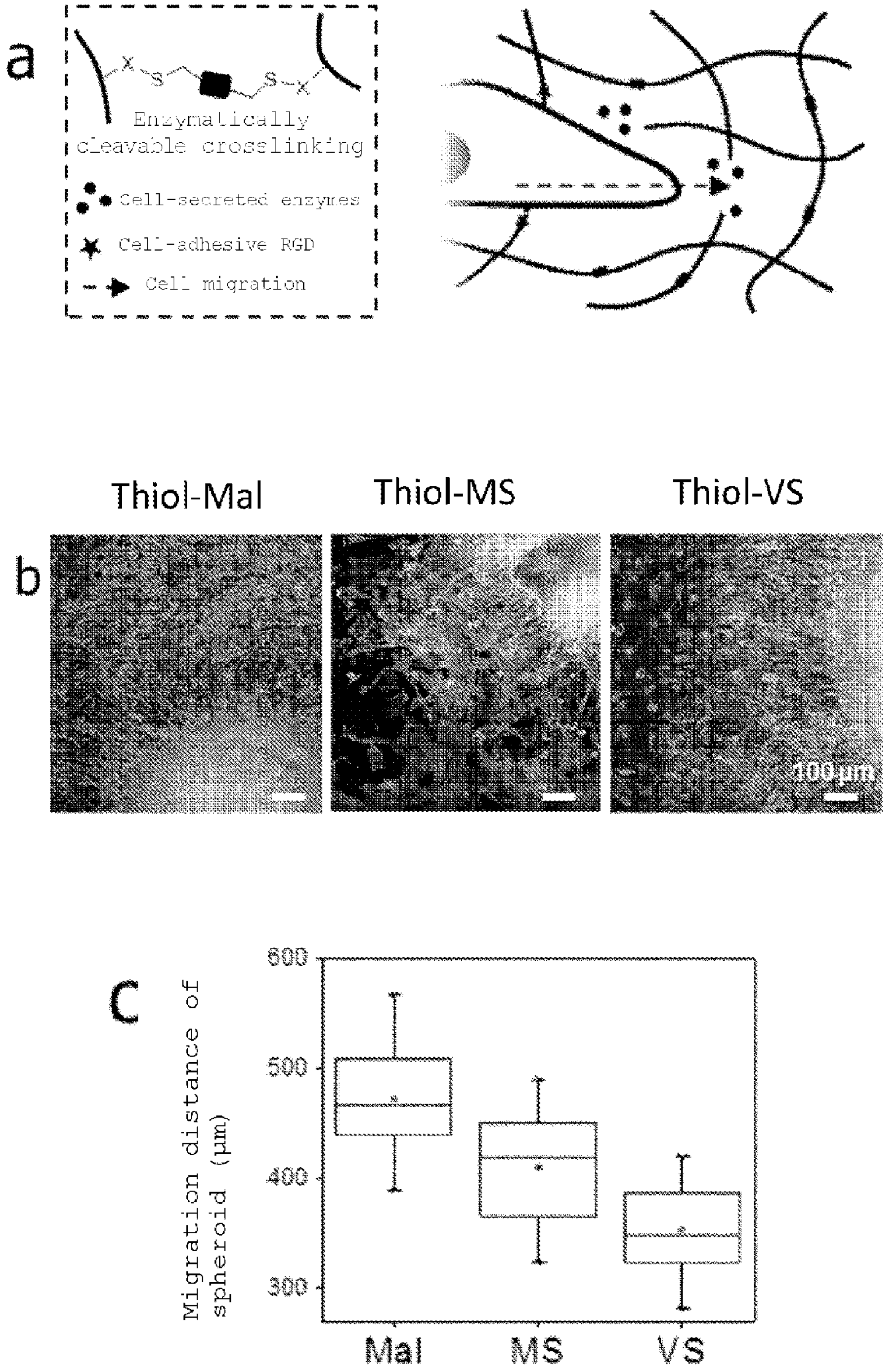
FIG. 9 (a) schemes of enzymatically cleavable gels used for encapsulating cell spheroids. (b-c) migration behavior of cells from encapsulated spheroids. The results of the migration test after 3-day culture showed that the migration distance in thiol-MS gels was in between. Staining: FITC-phalloidin (actin fibers), DAPI (nucleus)

In order to show that cells cultured in thiol-MS hydrogels remain functional, a migration assay was carried out. L929 fibroblast spheroids were encapsulated in the degradable thiol-MS hydrogels [A. Farrukh, J. I. Paez, A. del Campo, *Advanced Functional Materials* 2019, 29, 1807734], cultivated for 3 days, fixed and stained. The cell migration distance of the spheroid was quantified as an indicator of gel degradation and of the capacity for cell movement within the gel (FIG. 9*a-c*). The cells traveled a distance of d~425 μm. The results were compared with the results obtained for thiol-Mal and thiol-VS as materials for 3D cell encapsulation. The migration distance was ~470 μm for Mal and ~360 μm for VS systems (FIG. 9*c*). This result is due to the differences in the degree of crosslinking ($G'_{37^\circ C.}$=VS>MS>Mal; see FIG. 3*b*)) and in the hydrolytic stability (MS=VS>>Mal; FIG. 7). A lower degree of crosslinking or a more rapid degradation makes space for the cells, i.e. leads to longer migration pathways.

Figure 10:
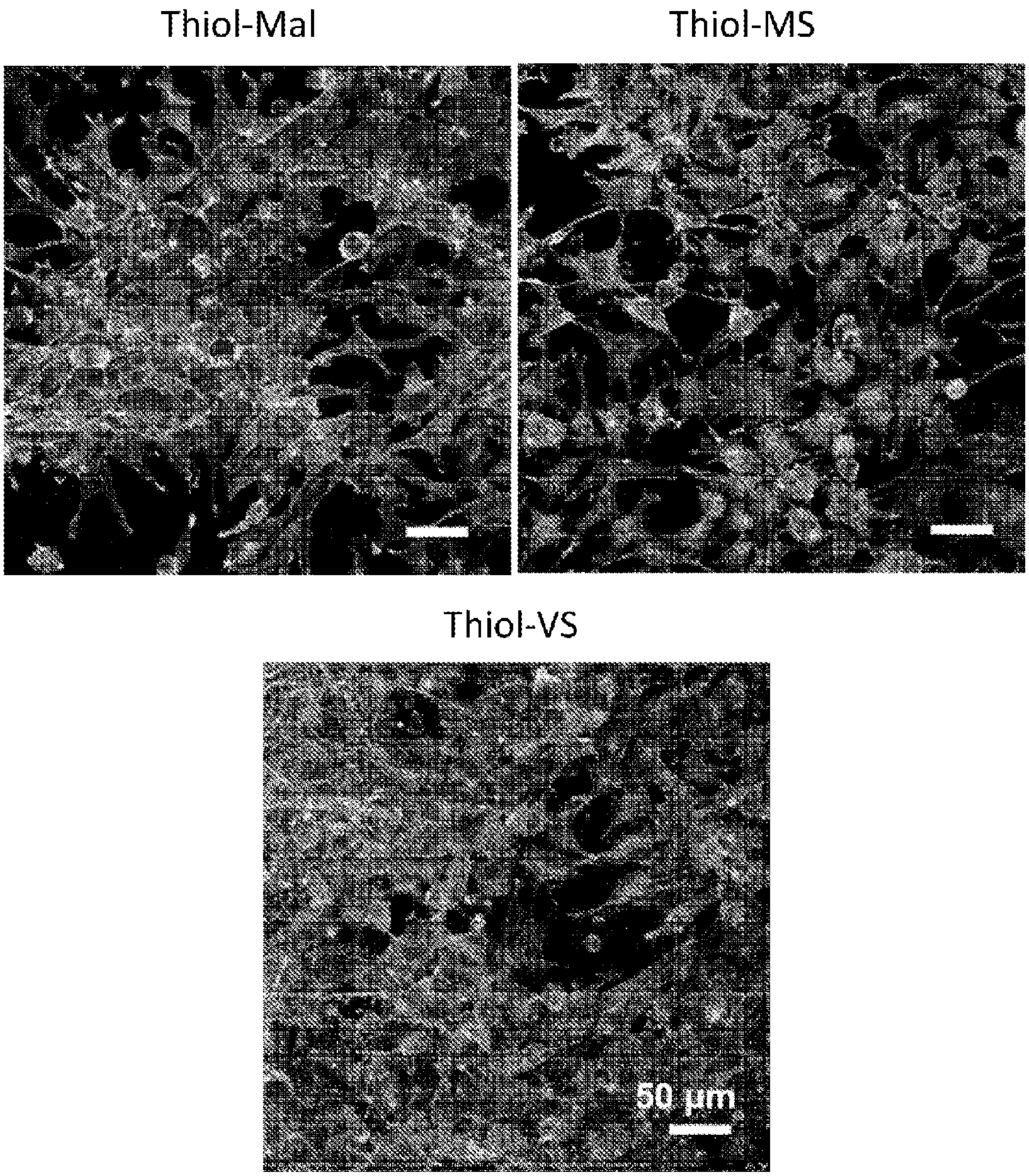
FIG. 10 morphology of individual cells (mouse fibroblast L929) enclosed in the various enzymatically cleavable thiol-X hydrogels after 3 days of cell cultivation. In comparison to the other systems, cells cultivated in thiol-MS hydrogels showed a more uniform distribution, less clustering or aggregation. Staining: FITC-phalloidin (actin fibers), DAPI (nucleus); the scale is 50 μm in each case.

Furthermore, after 3 days of incubation, the cells cultivated in Thiol-MS hydrogels were distributed more homogeneously in the gel and exhibited fewer instances of clustering than in the two other systems (see FIG. 10).

The thiol-MS reaction is suitable for the crosslinking of hydrogels in the context of cell encapsulation. This reaction achieves kinetics between thiol-Mal and thiol-VS systems and attains a high conversion. The resultant crosslinked units exhibit good hydrolytic stability and cytocompatibility. Under mild aqueous conditions, the MS-thiol reaction is orthogonal to alcohols, amines, carboxylic acids and acrylate functional groups [D. Zhang, N. O. Devarie-Baez, Q. Li, K. R. Lancaster, M. Xian, *Organic Letters* 2012, 14, 3396-3399. A. Farrukh, J. I. Paez, M. Salierno, A. del Campo, *Angew. Chem. Int. Ed.* 2016, 55, 2092-2096. A. Farrukh, J. I. Paez, M. Salierno, W. Fan, B. Berninger, A. del Campo, *Biomacromolecules* 2017, 18, 906-913], which allows this crosslinking mechanism to be employed with virtually any natural polymeric scaffold of interest in the biomedical sphere. The reactivity of the thiol-MS pairing can be regulated by the pH used and by the selection of different MS-aromatic substrates [N. Toda, S. Asano, C. F. Barbas, *Angew. Chem., Int. Ed.* 2013, 52, 12592-12596]. The combinations of all of these properties make thiol-MS a superior alternative to other reactive chemicals for 3D cell encapsulation.

TABLE 1

Gelling times of various gels measured in 10 mM HEPES buffer, T = 25° C., pH = 8-6.6

| Gel | pH 8.0 | pH 7.5 | pH 7.0 | pH 6.6 |
|---|---|---|---|---|
| Thiol-Mal | <1 s | 1-2 s | 2-3 s | 5-6 s |
| Thiol-MS | 3 s | 6 s | 12 s | 3.5 min |
| Thiol-VS | 8 min | 22 min | 88 min | 190 min |

TABLE 2

Reported second-order reaction rates for selected nucleophilic thiol-X couplings under mild aqueous conditions

| X | Reaction rate $k_2$ ($M^{-1}$ $s^{-1}$) | Source |
|---|---|---|
| Mal | 734.0 | F. Saito, H. Noda, J. W. Bode, ACS Chemical Biology 2015, 10, 1026-1033. |

TABLE 2-continued

Reported second-order reaction rates for selected nucleophilic thiol-X couplings under mild aqueous conditions

| X | Reaction rate $k_2$ ($M^{-1}$ $s^{-1}$) | Source |
|---|---|---|
| MS | 0.4-16.0 | X. Chen, H. Wu, C.-M. Park, T. H. Poole, G. Keceli, N. O. Devarie-Baez, A. W. Tsang, W. T. Lowther, L. B. Poole, S. B. King, M. Xian, C. M. Furdui, ACS Chemical Biology 2017, 12, 2201-2208. |
| VS | 0.08-1.0 | H. Wang, F. Cheng, M. Li, W. Peng, J. Qu, Langmuir 2015, 31, 3413-3421. |

TABLE 3

Gelling time determined in the bulk for thiol-MS hydrogels at different temperatures (5 wt % and 10 mM HEPES buffer)

| Gel | T: 45° C. | 25° C. | 15° C. | 5° C. |
|---|---|---|---|---|
| Thiol-MS (pH 7.0) | 7 s | 12 s | 22 s | 30 s |

TABLE 4

Gelling time determined in the bulk for thiol-MS hydrogels at different polymer content (10 mM HEPES buffer, pH 7.5, T = 25° C.)

| Gel | 10.0 wt % | 7.5 wt % | 5.0 wt % | 2.5 wt % | 1.3 wt % |
|---|---|---|---|---|---|
| Thiol-MS | 2-3 s | 4 s | 6 s | 10 s | 18 s |

TABLE 5

Swelling ratio in water of thiol-X hydrogels (5 wt % polymer fraction; n = 3)

| Gel | Swelling ratio [mg water/mg gel] | Relative value |
|---|---|---|
| Thiol-Mal | 48.8 ± 4.3 | 1.45 |
| Thiol-MS | 33.6 ± 1.0 | 1.00 |
| Thiol-VS | 35.3 ± 2.8 | 1.05 |

The invention claimed is:

1. A process for preparing a hydrogel, comprising:

a) preparing a composition comprising:

a1) at least one macromer comprising as functional groups at least two thiol groups, a2) at least one macromer comprising as functional groups at least two aromatic or heteroaromatic groups each substituted by at least one sulfonyl group, wherein the at least one macromer a1) or the at least one macromer a2) has at least three of the respective functional groups; and b) reacting the the at least one macromer a1) and the at least one macromer a2) via the respective functional groups to form a hydrogel, wherein the functional groups of the at least one macromer a2) are functional groups of the formula (1):

$$M—Ar—SO_2—R^1 \quad (1)$$

wherein:

Ar is an electron-deficient aryl group or electron-deficient heteroaryl group;

M is the connection to the macromer;

$R^1$ is $N(R^2)_2$, a straight-chain alkyl group having 1 to 20 C atoms or a branched or cyclic alkyl group having 3 to 20 C atoms, or an alkenyl or alkynyl group having 2 to 20 C atoms or a branched or cyclic alkyl group having 3 to 20 C atoms, wherein the alkyl, alkenyl or alkynyl group may be substituted in each case by one or more radicals $R^2$ and where one or more nonadjacent $CH_2$ groups may be replaced by O, $NR^2$, S, $R^2C{=}CR^2$, C≡C, C═O, C(═O)O or C(═O)$NR^2$, or is an aryl group or heteroaryl group which may be substituted in each case by one or more radicals $R^2$;

$R^2$, identical or different at each occurrence, is H, D, F, Cl, Br, I, $N(R^3)_2$, CN, $NO_2$, $OR^3$, $SR^3$, C(═O)$OR^3$, C(═O) $N(R^3)_2$, C(═O) $R^3$, a straight-chain alkyl group having 1 to 20 C atoms or an alkenyl or alkynyl group having 2 to 20 C atoms or a branched or cyclic alkyl group having 3 to 20 C atoms, wherein the alkyl, alkenyl or alkynyl group may be substituted in each case by one or more radicals $R^3$, where one or more nonadjacent $CH_2$ groups may be replaced by $R^3C{=}CR^3$, C≡C, C═O, $NR^3$, O, S, C(═O)O or C(═O)$NR^3$, or is an aryl group or heteroaryl group which may be substituted in each case by one or more radicals $R^3$; and $R^3$, identical or different at each occurrence, is H, D, F, OH, or an aliphatic, aromatic and/or heteroaromatic organic radical in which one or more H atoms may also be replaced by F.

2. The process as claimed in claim 1, wherein each of the at least one macromers a1) and a2) have an average molar mass of less than 500 kDa.

3. The process as claimed in claim 1, wherein each of the at least one macromers a1) and a2) contain 2, 3, 4, 5, 6, 7, 8, 9 or 10 of the respective functional groups.

4. The process as claimed in claim 1, wherein each of the at least one macromers a1) and a2) are based on poly(meth) acrylates, poly(meth)acrylamides, poly(meth)acrylic acid, polyHPMA, polyHEMA, polyethylene glycol, polyvinyl alcohol, polyurethane, polyvinylpyrrolidone, polyamides, poly(amido-amines), polyesters, polylactides, polyglycolic acid, poly(lactide-co-glycolide), polyanhydrides, poly(ortho)esters, polyacetals, poloxamers, poly-2-oxazolines, polyphosphazenes, polyglycerol, polyamines, polycarbonates, polyglutamic acid, polyaspartic acid, polyphosphonates, DNA, RNA, gelatin, polyhydroxyalkanoates, poly-gamma-glutamic acid, proteins, peptides, or polysaccharides.

5. The process as claimed in claim 1, wherein Ar is selected from the group consisting of nitrobenzenes, benzaldehydes, benzonitriles, benzoic esters, pyridines, pyrimidines, pyrazines, pyridazines, triazines, tetrazines, oxazoles, isoxazole, thiazoles, isothiazole, oxadiazoles, 1,2,3-thiadiazole, 1,2,4-thiadiazole, 1,2,5-thiadiazole, 1,3,4-thiadiazole, imidazole, pyrazole, triazoles, tetrazole, quinolines, isoquinolines, benzimidazole, benzoxazole, benzothiazole, benzopyridazine, benzopyrimidine, quinoxaline, benzotriazole, naphthalimide, purine, pteridine, indolizine and benzothiadiazole, wherein Ar may be substituted in each case additionally by one or more groups $R^2$.

6. The process as claimed in claim 1, wherein a macromer content of the composition is 1 to 30 wt % based on the at least one macromer a1) and the at least one macromer a2).

7. The process as claimed in claim 1, wherein gelling takes place under physiological conditions.

8. A hydrogel obtained as claimed in claim 1.

9. A composition for preparing a hydrogel, comprising components a1) and a2) as claimed in claim 1.

10. A kit for preparing a hydrogel, comprising components a1) and a2) as claimed in claim 1.

11. The process as claimed in claim 1, wherein each of the at least one macromers a1) and a2) is based on block copolymers of ethylene oxide (PEG) and propylene oxide (PPG).

12. The process as claimed in claim 1, wherein each of the at least one macromers a1) and a2) is based on polylysine or polyethylenimine.

13. The process as claimed in claim 1, wherein each of the at least one macromers a1) and a2) is based on poly-gamma-glutamic acid.

14. The process as claimed in claim 1, wherein each of the at least one macromers a1) and a2) is based on collagens, VPM, albumin or fibrin.

15. The process as claimed in claim 1, wherein each of the at least one macromers a1) and a2) is based on agarose, chitin, chitosan, chondroitin, mannan, inulin, dextran, cellulose, alginates or hyaluronic acid.

16. A process, comprising:

preparing a hydrogel as claimed in claim 1; and encapsulating cells in the hydrogel.

17. A process, comprising:

preparing a hydrogel as claimed in claim 1; and injecting the hydrogel into an organism, 3D printing with the hydrogel, or transporting an active ingredient to cells with the hydrogel.

18. The process as claimed in claim 1, wherein $R^3$, identical or different at each occurrence, is a straight-chain alkyl group having 1 to 20 C atoms in which one or more H atoms may also be replaced by F.

* * * * *